US011602311B2

(12) United States Patent
Mazar et al.

(10) Patent No.: US 11,602,311 B2
(45) Date of Patent: Mar. 14, 2023

(54) PULSE OXIMETRY SYSTEM

(71) Applicant: Murata Vios, Inc., Woodbury, MN (US)

(72) Inventors: Scott Thomas Mazar, Woodbury, MN (US); Carlos A. Ricci, Apple Valley, MN (US); Vladimir V. Kovtun, Inver Grove Heights, MN (US)

(73) Assignee: MURATA VIOS, INC., Woodbury, MN (US)

( * ) Notice: Subject to any disclaimer, the term of this patent is extended or adjusted under 35 U.S.C. 154(b) by 735 days.

(21) Appl. No.: 16/260,631

(22) Filed: Jan. 29, 2019

(65) Prior Publication Data

US 2020/0237315 A1 Jul. 30, 2020

(51) Int. Cl.
*A61B 5/00* (2006.01)
*A61B 5/024* (2006.01)
*A61B 5/1455* (2006.01)

(52) U.S. Cl.
CPC ........ *A61B 5/7225* (2013.01); *A61B 5/02416* (2013.01); *A61B 5/14551* (2013.01); *A61B 5/7282* (2013.01); *A61B 5/742* (2013.01); *A61B 5/746* (2013.01); *A61B 2560/0233* (2013.01)

(58) Field of Classification Search
CPC .............. A61B 5/7225; A61B 5/02416; A61B 5/14551; A61B 5/7282; A61B 5/742; A61B 5/746; A61B 2560/0233; A61B 5/725; A61B 5/726
See application file for complete search history.

(56) References Cited

U.S. PATENT DOCUMENTS

| 3,819,920 A | 6/1974 | Goldfischer |
| 3,993,862 A | 11/1976 | Karr |
| 4,193,393 A | 3/1980 | Schlager |
| 4,251,831 A | 2/1981 | Karnath |
| 4,314,105 A | 2/1982 | Mozer |

(Continued)

OTHER PUBLICATIONS

PCT International Search Report and Written Opinion in International Application No. PCT/US2020/015662, dated Apr. 17, 2020, 14 pages.

(Continued)

*Primary Examiner* — Devin B Henson
*Assistant Examiner* — Justin Xu
(74) *Attorney, Agent, or Firm* — Keating & Bennett, LLP

(57) ABSTRACT

In one aspect, a computer-implemented method includes receiving signals corresponding to wavelengths of light detected by an optical sensor placed in proximity to a patient's body, and for each received signal: separating the signal into an AC signal and a DC signal; separating the AC signal into component signals; analyzing the component signals through a fractional phase transformation to identify a desired component signal and harmonic signals associated with the desired component signal; smoothing the desired component signal, the harmonic signals, and the DC signal; and combining the smoothed desired component signal, the smoothed harmonic signals, and the smoothed DC signal to generate a modulation signal. A modulation ratio signal is generated based on the modulation signals derived from the signals, and a peripheral oxygen saturation (SpO2) of the patient's body is determined based on the modulation ratio signal.

42 Claims, 8 Drawing Sheets

(56) References Cited

U.S. PATENT DOCUMENTS

| | | |
|---|---|---|
| 4,461,022 A | 7/1984 | Slagley |
| 4,633,884 A | 1/1987 | Imai |
| 4,680,797 A | 7/1987 | Benke |
| 4,736,295 A | 4/1988 | Lachiver |
| 5,115,240 A | 5/1992 | Fujiwara |
| 5,230,038 A | 7/1993 | Fielder |
| 5,392,044 A | 2/1995 | Kotzin |
| 5,486,867 A | 1/1996 | Hsu |
| 5,500,874 A | 3/1996 | Terrell |
| 5,730,142 A | 3/1998 | Sun |
| 5,749,367 A | 5/1998 | Gamlyn |
| 5,778,881 A | 7/1998 | Sun |
| 5,828,995 A | 10/1998 | Satyamurti |
| 5,999,561 A | 12/1999 | Naden |
| 6,008,618 A | 12/1999 | Bose |
| 6,020,840 A | 2/2000 | Ong |
| 6,347,125 B1 | 2/2002 | Dent |
| 6,389,308 B1 | 5/2002 | Shusterman |
| 6,429,693 B1 | 8/2002 | Staszewski |
| 6,456,651 B1 | 9/2002 | Pilozzi |
| 6,470,210 B1 | 10/2002 | Chen |
| 6,475,245 B2 | 11/2002 | Gersho |
| 6,510,339 B2 | 1/2003 | Kovtun |
| 6,512,944 B1 | 1/2003 | Kovtun |
| 6,606,056 B2 | 8/2003 | Brogden |
| 6,618,617 B2 | 9/2003 | Chen |
| 6,687,674 B2 | 2/2004 | Suzuki |
| 6,718,038 B1 | 4/2004 | Cusmario |
| 6,782,058 B1 | 8/2004 | Nayler |
| 6,785,700 B2 | 8/2004 | Masud et al. |
| 6,791,482 B2 | 9/2004 | Koyanagi |
| 6,838,912 B1 | 1/2005 | Chou |
| 6,914,935 B2 | 7/2005 | Eklof |
| 6,917,830 B2 | 7/2005 | Paireddy |
| 6,925,324 B2 | 8/2005 | Shusterman |
| 6,976,046 B2 | 12/2005 | Guevorkian et al. |
| 7,054,792 B2 | 5/2006 | Frei |
| 7,058,548 B2 | 6/2006 | Pupalaikis |
| 7,088,276 B1 | 8/2006 | Wegener |
| 7,171,269 B1 | 1/2007 | Addison |
| 7,200,435 B2 | 4/2007 | Ricci |
| 7,254,187 B2 | 8/2007 | Mohan |
| 7,346,640 B2 | 3/2008 | Katayama |
| 7,372,929 B2 | 5/2008 | Macinnis |
| 7,480,416 B2 | 1/2009 | Liao et al. |
| 7,506,239 B2 | 3/2009 | Sudhakar |
| 7,640,055 B2 | 12/2009 | Geva |
| 7,702,502 B2 | 4/2010 | Ricci et al. |
| 7,706,992 B2 | 4/2010 | Ricci et al. |
| 7,912,378 B2 | 3/2011 | Tian |
| 8,010,347 B2 | 8/2011 | Ricci |
| 8,086,304 B2 | 12/2011 | Brockway et al. |
| 8,386,244 B2 | 2/2013 | Ricci |
| 8,595,278 B2 | 11/2013 | Han et al. |
| 9,209,782 B2 | 12/2015 | Ricci |
| 9,530,425 B2 | 12/2016 | Ricci et al. |
| 10,039,463 B1* | 8/2018 | Selvaraj ............. A61B 5/14551 |
| 2001/0023396 A1 | 9/2001 | Gersho |
| 2002/0178006 A1 | 11/2002 | Suzuki |
| 2004/0054297 A1 | 3/2004 | Wingeier |
| 2004/0073098 A1 | 4/2004 | Geva |
| 2004/0078160 A1 | 4/2004 | Frei |
| 2004/0093192 A1 | 5/2004 | Hasson |
| 2004/0174935 A1 | 9/2004 | Macinnis |
| 2004/0181399 A1 | 9/2004 | Gao |
| 2004/0184568 A1 | 9/2004 | Kobylinski |
| 2004/0264622 A1 | 12/2004 | Walsh |
| 2005/0107836 A1 | 5/2005 | Noren |
| 2005/0197073 A1 | 9/2005 | Klemmer |
| 2006/0200034 A1 | 9/2006 | Ricci |
| 2006/0200035 A1 | 9/2006 | Ricci |
| 2007/0219455 A1 | 9/2007 | Wong |
| 2008/0002775 A1 | 1/2008 | Ricci |
| 2008/0015452 A1 | 1/2008 | Ricci |
| 2008/0181332 A1 | 7/2008 | Tian |
| 2012/0179001 A1 | 7/2012 | Taylor et al. |
| 2014/0278382 A1* | 9/2014 | Ricci ................. H03H 17/0201 |
| | | 704/206 |
| 2014/0289297 A1 | 9/2014 | Ricci |
| 2015/0302539 A1 | 10/2015 | Mazar et al. |
| 2016/0228060 A1 | 8/2016 | Mazar et al. |
| 2018/0213859 A1 | 8/2018 | Laplante et al. |
| 2019/0099114 A1* | 4/2019 | Mouradian .......... A61B 5/0002 |

OTHER PUBLICATIONS

Ronald,, "The Fourier Transform and its Applications", McGraw-Hill, (2000), 29 pages.

Olivier et al., "Inference in Hidden Markov Models", Springer, (2005), 17 pages.

Cetin et al., "Compression of Digital Biomedical Signals", The Biomedical Engineering Handbook: Second Edition, Jose12h D. Bonzino, Ed. CRC Press LLC, (2000),Chapter 54, 13 pages.

Chen et al., "Multiplierless Approximations of Transforms with Adder Constraing", IEEE Signal Processing Letters vol. 9, No. 11, (Nov. 2002), pp. 344-347.

Duda et al., "Pattern Classification, Second Ed.", (2001), 30 pages.

Elliott et al., "Hidden Markov Models", Springer-Verlag, (1995), 11 pages.

Fliege, "Multirate Digital Signal Processing", Wiley, (1994), 11 pages.

Golub et al., "Matrix Computations, Third Ed.", Hopkins, (1996), 13 pages.

Kotteri et al., "Design of Multiplierless, High-Performance, Wavelet Filter Banks with Image Compression Applications", IEEE Transactions on Circuits and Systems, vol. 51 No. 3, Mar. 2004., (483-494).

MacDonald et al., "Hidden Markov and Other Models for Discrete-valued Time Series", Chapman, (1997), 12 pages.

Openheim et al., "Discrete-Time Signal Processing, Second Ed.", Wiley, (1999), 21 pages.

Ozaktas et al., "The Fractional Fourier Transform", Wiley, (2001), 25 pages.

Stoica et al., "Spectral Analysis of Signals", Prentice-Hall, (2005), 17 pages.

Strang et al., "Wavelets and Filter Banks", Welleslei, (1997), 11 pages.

Vapnik, "The Nature of Statistical Learning Theory, Second Ed.", Springer, (2000), 13 pages.

Vetterli et al., "Wavelets and Subband Coding", Prentice-Hall, (1995), 16 pages.

Xue et al., "Late Potential Recognition by Artificial Neural Networks", IEEE Trans Bio Eng, vol. 44, (1997), 132-143.

* cited by examiner

PULSE OXIMETRY SYSTEM

BACKGROUND

This disclosure relates to pulse oximetry.

Pulse oximetry is used to estimate the time-local average percent oxygen saturation present in the blood of a patient's periphery ($SpO_2$) based upon photoplethysmogram (PPG) signals received from a sensor. The basic principle of estimating $SpO_2$ via PPG relies upon the relationship between the relative attenuation of photonic transmission through and/or reflection from the blood volume in tissue at different wavelengths of light, in response to levels of oxygenation in the blood. Typically, two wavelengths of light are used, e.g., wavelengths in the red and infrared (IR) portions of the spectrum. For each wavelength, PPG is obtained at a location on the patient's periphery, e.g., a fingertip or an earlobe here forward referred to as the red PPG and the IR PPG respectively and without loss of generality. Light sources and detectors would typically be implemented using readily-available light-emitting diodes (LEDs) and photodiodes, respectively. A ratiometric measure is then derived from parameters extracted from these two PPGs, which due to the relative attenuation characteristic of the two wavelengths, leads to a generally well-behaved, monotonic mapping to $SpO_2$ that is valid for patients over a broad population.

The PPG signal is primarily characterized by two components: a DC component corresponding to the bulk light transmission in the tissue, and an AC component corresponding to the modulation of transmission due to blood flow (and the change in blood volume due to that flow) upon each cardiac pulse. The raw modulation of transmission is measured by detecting the raw amplitude of the AC component of the PPG signal. Normalization of this raw amplitude measure with a measure of the DC component then produces a percentage-modulation term.

Taking the percentage-modulation term from the red PPG signal and dividing it by that of the IR PPG signal forms a normalized ratio $R_N$ that is mapped to $SpO_2$ values. The mapping of $R_N$ to $SpO_2$ values may be determined through a calibration procedure that is typically performed in a clinical setting (e.g., a hypoxia laboratory), where values of $R_N$ are collected simultaneously with reference measures of arterial oxygen saturation ($SaO_2$). A set of ($R_N$, $SaO_2$) value pairs is collected over a set of human subjects to each of whom a controlled set of hypoxia states is induced (while being supervised for safety), thus establishing a range of corresponding $SaO_2$ values. A mapping is then developed over the range of ($R_N$, $SaO_2$) value pairs, e.g., using a lookup table or a polynomial fit. Applying this map to values of $R_N$ then produces corresponding values of $SpO_2$, taken as an estimate of $SaO_2$. Typically, values of $SpO_2$ are resolvable with accuracy acceptable in the field over a range of roughly 70% to 100%.

The AC component of the PPG signal is comprised of pulses correlated to the vascular blood flow, with peaks and cyclic behavior according to the cardiac cycle. Because of this, the pulse rate (PR) may be derived directly from this component. Many methods are available, from simple peak detection and interval counting to sophisticated rate detection methods. Often smoothing is applied to compute a time-local average of the pulse rate.

A working realization of the $SpO_2$ measure based only upon the above basic principles may be made in a fairly straightforward manner, for example, using classic filtering and energy detection methods to perform the extraction of AC and DC components and measuring of the AC amplitude. Such a basic method will generally work as long as conditions are favorable, e.g., the signal to noise ratio (SNR) is relatively high (more specifically, when the percentage-modulation is relatively large compared to background noise or interference sources).

In practice, challenges can arise due to various conditions that reduce SNR. For example, the patient's own respiration will modulate the PPG, producing a separate cyclical interference component within the AC component signal, sometimes with more raw power than that of the desired pulse-mediated modulation. Also, motion at the extremity associated with the optical sensing point can have a similar modulating effect on the PPG, producing either a cyclical or transient interference term depending upon the motion. In addition, patients can exhibit low perfusion, which lowers the percentage-modulation and hence the amplitude of the AC signal relative to background noise and/or interference terms. Such conditions of lowered SNR tend to bias the normalized ratio $R_N$ toward unity (which in practice often tends to bias the mapped $SpO_2$ values toward the vicinity of 85%), which presents a real performance challenge for maintaining $SpO_2$ accuracy over the desired range across a broad patient population.

SUMMARY

This disclosure describes systems and techniques related to pulse oximetry. The system processes PPG signals simultaneously through parallel channels. For each channel, the system performs input processing of the PPG signal, analytic wavelet bank processing, quarter-phase (QP) domain harmonic detection and tracking, and QP-domain harmonic state vector filtering and amplitude statistics processing. Input processing of the PPG signal includes sample interpolation to increase the sample rate of the system to support the frequency resolution needed for the harmonic processing, filtering to reduce effects of out-of-band artifacts and to generally improve SNR, and band separation of the PPG signal into basic AC and DC components. Analytic wavelet bank processing separates the AC components into $n_B$ component bands each with substantially increased SNR. QP-domain harmonic detection and tracking includes QP transformation and state vector generation, periodicity detection for estimation of per-QP pulse interval based upon harmonic pattern identification in QP state space, and tracking of harmonic parameters in QP space for $n_H$ harmonics. QP-domain harmonic state vector filtering and amplitude statistics processing includes individual per-harmonic filtering of parameters (QP-space linear smoothing) to form robust moving measures of harmonic amplitude, QP-synchronized filtering of DC components of the PPG signal, combination of harmonic amplitude to form robust measure of the AC component pulse amplitude, combination of the AC information with the DC information to form robust moving measures of the normalized percent-fraction PPG pulse modulation and moving measure of the normalized modulation ratio, and QP-synchronized filtering to form the instantaneous pulse interval. The system then performs statistical filtering of the moving measure of the normalized modulation ratio to form a smoothed moving estimate of the normalized modulation ratio and statistical filtering of the instantaneous pulse interval to form a smoothed moving estimate of instantaneous pulse interval. The system then maps the smoothed moving estimate of the normalized modulation ratio to output SpO$_2$ and maps the smoothed moving estimate of instantaneous pulse interval to output pulse rate.

The system can provide accurate SpO$_2$ estimates for small percentage-modulation amplitude levels caused by a) relatively low perfusion (low local blood volume) and b) relatively dark skin (high amount of attenuation of raw signal) by using harmonic QP components that have individually high SNR and averaging tracked harmonic QP parameters in QP time to further increase SNR. The system can be resistant to cardio-pulmonary coupling artifact and motion artifact by using periodicity pattern detection to track the periodic component due to pulse and to reject components due to breath artifact and motion artifact.

In general, in one innovative aspect, a system includes an optical sensor configured to detect light, a display apparatus, one or more data processing apparatus coupled with the optical sensor and the display apparatus, and a non-transitory computer readable storage medium encoded with a computer program. The program includes instructions that when executed by the one or more data processing apparatus cause the one or more data processing apparatus to perform operations. The operations include receiving a first signal corresponding to a first wavelength of light detected by the optical sensor placed in proximity to a patient's body and receiving a second signal corresponding to a second wavelength of light detected by the optical sensor. For each received signal of the first signal and the second signal, the operations include separating the signal into an AC signal and a DC signal; separating the AC signal into component signals, wherein each of the component signals represents a frequency-limited band; identifying, from the component signals or from another source such as a heart rate detector based upon an ECG, an underlying pulse rate; analyzing the component signals through a fractional phase transformation to identify a desired component signal and harmonic signals associated with the desired component signal, all associated locally in time with the underlying pulse rate; smoothing the desired component signal, the harmonic signals, and the DC signal; and combining the smoothed desired component signal, the smoothed harmonic signals, and the smoothed DC signal to generate a modulation signal. The operations include generating a modulation ratio signal based on the modulation signal derived from the first signal and the modulation signal derived from the second signal; determining peripheral oxygen saturation (SpO2) of the patient's body based on the modulation ratio signal; and causing the display apparatus to display a value representing the determined SpO2 of the patient's body.

In another aspect, an apparatus includes a non-transitory computer readable storage medium encoded with a computer program. The program includes instructions that when executed by the one or more data processing apparatus cause the one or more data processing apparatus to perform operations. The operations include receiving a first signal corresponding to a first wavelength of light detected by an optical sensor placed in proximity to a patient's body and receiving a second signal corresponding to a second wavelength of light detected by the optical sensor. For each received signal of the first signal and the second signal, the operations include separating the signal into an AC signal and a DC signal; separating the AC signal into component signals, wherein each of the component signals represents a frequency-limited band; identifying, from the component signals or from another source such as a heart rate detector based upon an ECG, an underlying pulse rate; analyzing the component signals through a fractional phase transformation to identify a desired component signal and harmonic signals associated with the desired component signal, all associated locally in time with the underlying pulse rate; smoothing the desired component signal, the harmonic signals, and the DC signal; and combining the smoothed desired component signal, the smoothed harmonic signals, and the smoothed DC signal to generate a modulation signal. The operations include generating a modulation ratio signal based on the modulation signal derived from the first signal and the modulation signal derived from the second signal and determining peripheral oxygen saturation (SpO2) of the patient's body based on the modulation ratio signal.

In another aspect, a method includes receiving a first signal corresponding to a first wavelength of light detected by an optical sensor placed in proximity to a patient's body and receiving a second signal corresponding to a second wavelength of light detected by the optical sensor. For each received signal of the first signal and the second signal, the operations include separating the signal into an AC signal and a DC signal; separating the AC signal into component signals, wherein each of the component signals represents a frequency-limited band; identifying, from the component signals or from another source such as a heart rate detector based upon an ECG, an underlying pulse rate; analyzing the component signals through a fractional phase transformation to identify a desired component signal and harmonic signals associated with the desired component signal, all associated locally in time with the underlying pulse rate; smoothing the desired component signal, the harmonic signals, and the DC signal; and combining the smoothed desired component signal, the smoothed harmonic signals, and the smoothed DC signal to generate a modulation signal. The method includes generating a modulation ratio signal based on the modulation signal derived from the first signal and the modulation signal derived from the second signal and determining peripheral oxygen saturation (SpO2) of the patient's body based on the modulation ratio signal.

Various other functions and benefits of such a system will be apparent from the foregoing detailed description and claims.

DESCRIPTION OF DRAWINGS

Like reference numbers and designations in the various drawings indicate like elements.

DETAILED DESCRIPTION

Figure 1:
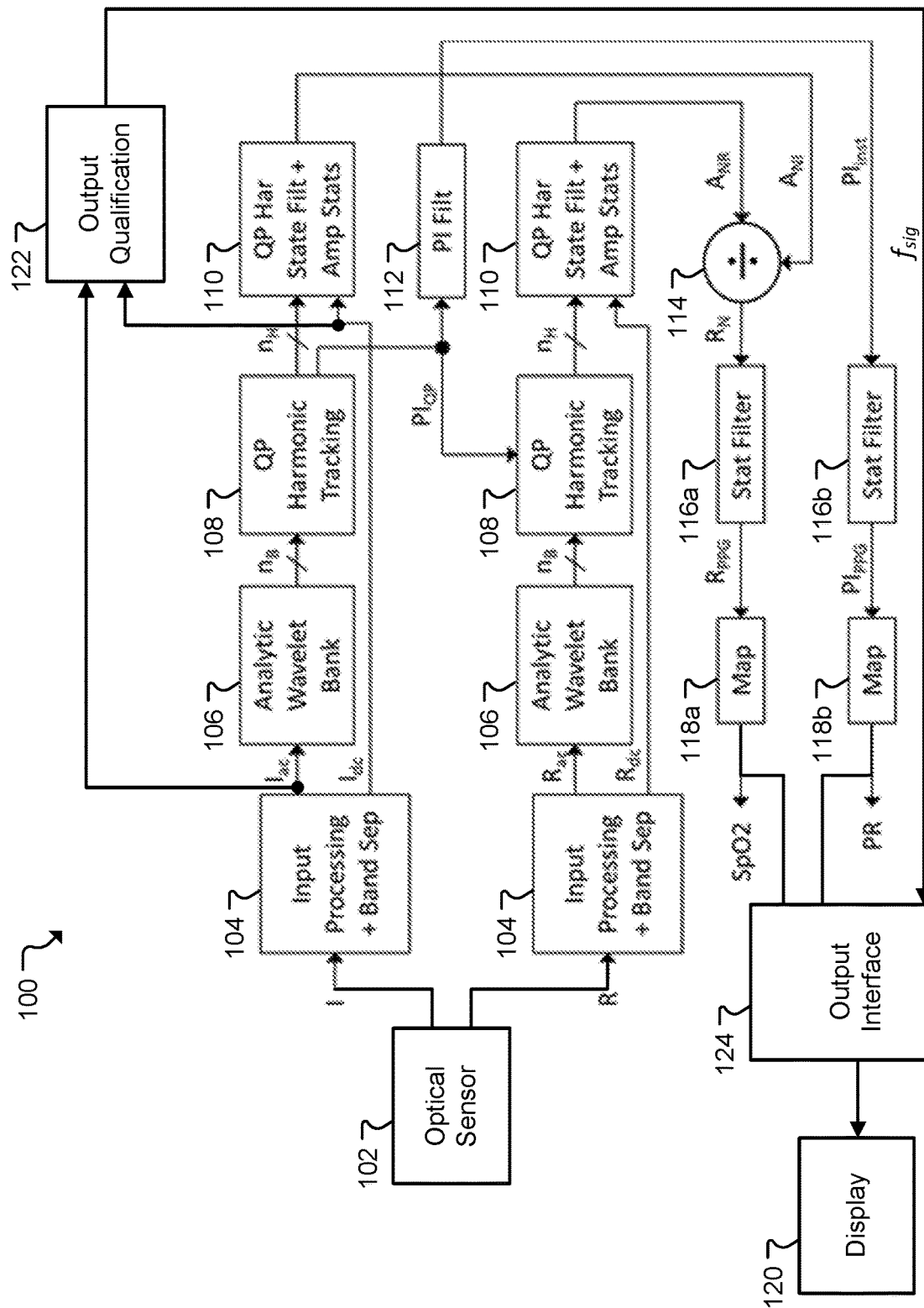
FIG. 1 is a block diagram showing an example of a pulse oximetry system.

FIG. 1 is a block diagram showing an example of a pulse oximetry system 100. The system 100 includes electronic components, e.g., hardware and/or software that facilitate pulse oximetry. The system 100 estimates the time-local average percent oxygen saturation present in the blood of a patient's periphery ($SpO_2$) and the time-local average of the patient's pulse rate (PR). In some implementations, portions of the system 100 are included in a patient monitoring device that can continuously collect physiological vital signs data, such as electrocardiogram (ECG), heart rate, respiratory rate, oxygen saturation, blood pressure, temperature, and pulse rate. Examples of patient monitoring devices include chest sensors, such as those described in U.S. Publication No. 2015/0302539, filed Oct. 22, 2015, titled "Patient Care and Health Information Management Systems and Methods" and U.S. Publication No. 2016/0228060, filed Feb. 9, 2016, titled "Patient Worn Sensor Assembly," and other sensor assemblies that connect with peripheral devices, such as the sensor assembly described in U. S. Publication No. 2018/0213859, filed Jan. 25, 2018, titled "Sensor Connection Assembly for Integration with Garment," the disclosures of which are hereby incorporated by reference in their entirety. In some implementations, portions of the system 100 are included in a monitoring station that analyzes and displays physiological vital signs data using signals received from one or more peripheral devices, such as a chest sensor, a fingertip probe, an earlobe probe, or a non-invasive blood pressure (NIBP) cuff. Examples of monitoring stations include a bedside monitor and a central server station which are also described in U.S. Publication No. 2015/0302539.

The system 100 includes an optical sensor 102 that generates photoplethysmogram (PPG) signals (denoted as signals I and R) corresponding to two wavelengths of light, e.g., the infrared and red portions of the spectrum, sensed by the optical sensor 102 at a location on the patient's periphery, e.g., a fingertip or an earlobe. The optical sensor 102 can be, for example, affixed to the patient's fingertip or earlobe. The sensor 102 can include light sources and detectors implemented using, for example, light-emitting diodes (LEDs) and photodiodes, respectively. The sensor 102 can continuously acquire PPG to facilitate continuous oxygen saturation and pulse rate monitoring. The sensor 102 can sample PPG at a rate of 74 Hz to 76 Hz so that 50 Hz and 60 Hz illumination interference can be filtered out.

The system 100 processes the I and R signals simultaneously through parallel channels. For each channel, the system 100 includes an input processing and band separation unit 104, an analytic wavelet bank 106, a quarter-phase (QP) domain harmonic detection and tracking unit 108, and a QP-domain harmonic state vector filtering and amplitude statistics processing unit 110. U.S. Pat. No. 7,702,502 filed Feb. 23, 2006, titled "Apparatus for Signal Decomposition, Analysis and Reconstruction," U.S. Pat. No. 7,706,992 filed Feb. 23, 2006, titled "System and Method for Signal Decomposition, Analysis and Reconstruction," U.S. Pat. No. 8,086,304 filed Nov. 26, 2008, titled "Physiological Signal Processing to Determine a Cardiac Condition," and U.S. Pat. No. 9,530,425 filed Mar. 17, 2014, titled "Method and Apparatus for Signal Decomposition, Analysis, Reconstruction and Tracking" include disclosures of techniques applicable to the processing of the I and R signals when taken as signals generally having quasi-periodic components. The entire contents of U.S. Pat. Nos. 7,702,502, 7,706,992, 8,086,304, and 9,530,425 are hereby incorporated by reference.

For systems having ratiometric measures, the two processing channels may have processing dynamics (e.g., filtering, delays, etc.) that are as similar as possible, so that dynamic changes in the sensing system (e.g., optical sensor 102) will ripple through the processing channels in a time-aligned and phase-aligned manner. Thus, as the ripple effects arrive at the ratio point together, they tend to be cancelled out and thereby minimized at the output, providing robustness against transients. For this reason, system 100 may maintain symmetry between the parallel channels at every point to ensure synchronization of delays between the I and R channels and between the AC and DC channels.

Figure 2:
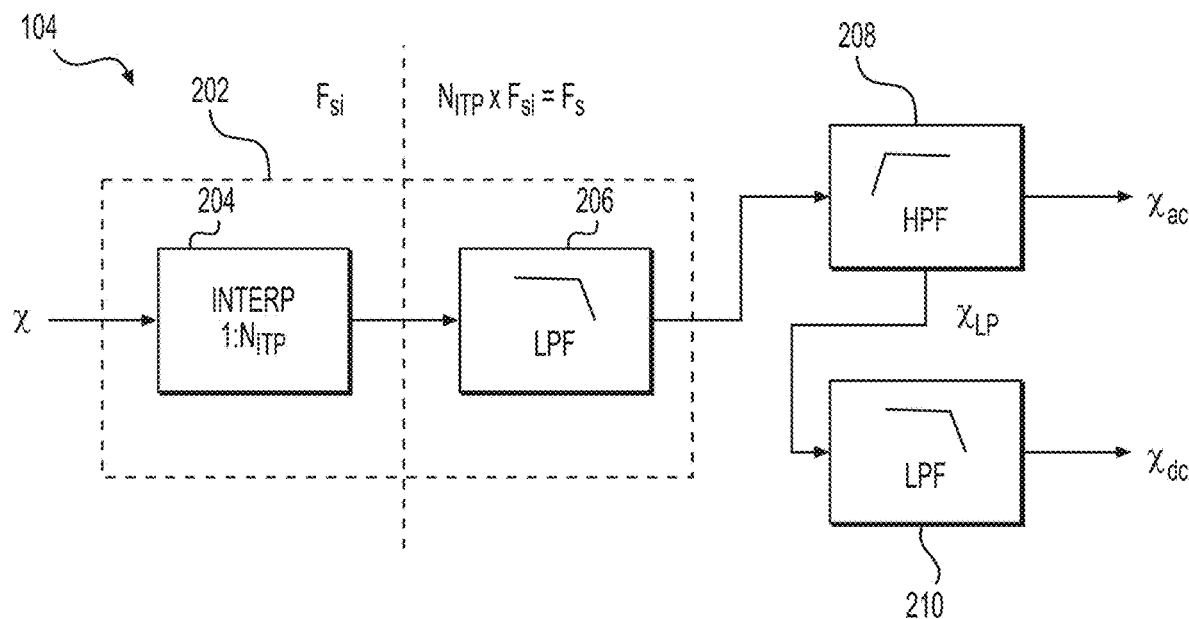
FIG. 2 is a block diagram showing an example of an input processing and band separation unit.

In some implementations, the input processing and band separation unit 104 performs sample interpolation to increase the sample rate of the PPG signal to support the frequency resolution needed for the subsequent QP-domain harmonic processing, performs filtering to reduce effects of out-of-band artifacts and to generally improve SNR, and performs band separation of the PPG signal into AC and DC components. FIG. 2 is a block diagram showing an example of the input processing and band separation unit 104. The input processing and band separation unit 104 reduces out-of-band interference and artifacts in the raw PPG signal by bandpass filtering the AC component and multi-stage lowpass filtering the DC component.

In some implementations, the input processing and band separation unit 104 includes a bandlimited interpolation unit 202. The bandlimited interpolation unit 202 includes an interpolation unit 204 and a lowpass filter 206 to perform bandlimited interpolation of the PPG signal to attenuate high-frequency (HF) interference and to raise the input sample rate by a factor $N_{ITP}$. In some implementations, the interpolation unit is bypassed, so that effectively $N_{ITP}=1$.

As described in more detail below with respect to the QP-domain harmonic detection and tracking unit 108, the system 100 performs extraction and tracking of the time-varying harmonic components of the pulsatile-modulation portion of the PPG signal. The highest frequency $f_{HI}$ to be resolved (and therefore the system passband) is determined by the product of 1) the number of harmonics $n_H$ to be resolved and 2) the highest pulse rate $r_{HI}$ at which the highest harmonic is to be resolved. The lowpass filter 206 with a corner substantially near to this frequency can attenuate out-of-band high-frequency interference terms and increase the system SNR.

At normal pulse rates, e.g., ranging from normal sinus rhythm (NSR) to mild exercise (~120 beats per minute (BPM)), the bulk of the harmonic power (~90%) is substantially contained in the first three harmonics of the PPG signal. Above this range, the harmonic power drops steadily with increasing pulse rate so that above ~180 BPM the signal is mostly first-harmonic, i.e., the morphology becomes quasi-sinusoidal. As a result, $$f_{HI}=n_H \times r_{HI}=3 \times 120 \text{ BPM}=360 \text{ BPM}=6 \text{ Hz}.$$

Frequency $f_{HI}$, being the highest signal frequency of interest, nominally defines the highest-frequency wavelet band needed in the analytic wavelet bank 106 (described below) for extracting harmonic content from the PPG signal. As described in the patents incorporated by reference herein relating to techniques applicable to the processing of the I and R signals, the analytic wavelet bank 106 typically restricts the scaling interval widths to integer numbers of samples to maintain high computational efficiency. This restriction can lead to increasingly coarse frequency resolution at increasingly high wavelet center frequencies, i.e., the wavelet band center frequencies are increasingly quantized, due to the shrinking scales becoming increasingly affected by the time quantization imposed by the integer-sample scale widths. Adding to the challenge is the desire to maintain sufficient resolution at higher frequencies to maintain separation of each harmonic component to be resolved.

The nominal input sample rate of $F_{si}=75$ Hz for the raw PPG signal would lead to band-center quantization sufficient to produce inter-band response gaps that are large enough to not be able to resolve harmonic amplitudes at the highest pulse rates without ambiguity. To resolve this issue, in some implementations, the input processing and band separation unit 104 interpolates samples for processing by the analytic wavelet bank 106 by resampling the input signal stream (i.e., "up-sampling"). The bandlimited interpolation unit 202 provides bandlimited interpolation implemented through a combination of zero-insertion by the interpolation unit 204 followed by synchronized lowpass filtering by lowpass filter 206 to "fill in" the added zeros. The lowpass filter's corner frequency can be set at the highest expected signal frequency to further provide bandlimiting so as to optimize SNR against high-frequency noise and artifacts. This up-sampling provides for up-sampled rates $F_s$ at integer multiples $N_{ITP}$ of the raw input sample rate $F_{si}$. An up-sampling factor of $N_{ITP}=3$ may be used to provide the frequency resolution needed to properly resolve a third harmonic at $f_{HI}=6$ Hz, thus yielding a nominal internal wavelet processing sample rate of $F_s=225$ Hz.

The interpolation unit 204 may use zero-insertion, which is a computationally-efficient operation. The lowpass filter 206 is also implemented with high computational efficiency by using a scaled-integral kernel operator as described in U.S. Pat. No. 7,706,992. The interpolation unit 204 up-samples the raw PPG signal x by a factor of $N_{ITP}$ by insertion of ($N_{ITP}-1$) zero-valued samples in between each successive input sample. This is followed by the synchronized lowpass filter 206 implemented using a scaled-integral kernel. As described in U.S. Pat. No. 7,706,992, the frequency response of this digital scaled-integral kernel approximately follows a sinc function in magnitude, having nulls at integer multiples of ($F_s/w$), where w is the integrator scale parameter in samples and $F_s$ is the up-sampled sample rate. Setting w to an integer multiple of $N_{ITP}$ places a response null at the new sample rate, thereby eliminating any time-domain ripple artifacts introduced by the zero-interpolation process. The scale is thus set according to the formula:

$$w_p = N_{ITP} \cdot \text{round}(F_s/(N_{ITP} \cdot f_{HI}/k_{6\ dB})),$$

which yields the closest scale in samples (sampled at rate $F_s$) that is an integer multiple of $N_{ITP}$ to place the –6 dB lowpass corner frequency as close as possible to $f_{HI}$, where the factor $k_{6\ dB}$ is the ratio of the –6 dB point to the first frequency-response null of the lowpass filter 206 and depends upon the order of the scaled integrator operator.

The overall smoothness and out-of-band HF rejection of the final interpolated result is then controlled by the size of integer factor ($w_p/N_{ITP}$), i.e., the number of input samples within the scale of the integrator, and the order of the scaled integrator. A second-order integrator kernel may provide a sufficient degree of smoothness and out-of-band HF rejection. For a nominal input sample rate of $F_{si}=75$ Hz, the following parameters for the bandlimited interpolator scaled integral may be used:

TABLE 1

| $N_{ITP}$ = 3, $F_s$ = 225 Hz, $f_{HI}$ = 6 Hz | | |
|---|---|---|
| $w_p$ | $N_i$ | $D_{ITP}$ |
| 18 | 2 | 17 | where $k_{6\ dB}=0.44295$ for $N_i=2$, and $D_{ITP}$ is the intrinsic delay in samples at rate $F_s$.

The AC component of the up-sampled and bandlimited PPG signal is separated through a highpass filter 208. The highpass filter 208 is designed to remove the large DC offset associated with the raw optical transmission in the PPG signal, giving an output that is centered on a zero baseline, and to reject as much low-frequency artifact as is practical below the lower nominal pulse rate band edge (in some implementations, 30 BPM or 0.5 Hz, corresponding to a pulse interval of 2 seconds beat-to-beat). In some implementations, the highpass filter 208 can have a linear-phase response. Given the size of the time scale, the highpass filter 208 can have a minimum-phase response to minimize time lags in the system due to the filter's intrinsic group delay. Using a recursive-form IIR filter topology may lead to a memory-efficient filter architecture. A second-order response can be used to provide good stability and sufficient rejection in the stop band. The highpass filter 208 is specified according to the following analog-domain transfer function:

$$H_{HP}(s) = \frac{s^2}{s^2 + \frac{\omega_c}{Q}s + \omega_c^2}$$

where $\omega_c$ controls the corner frequency (in radians/sec) and Q controls the resonance of the filter at the corner. The value of Q can be set to, for example, Q=0.720, to maximize response flatness in the passband and response sharpness at the corner, while minimizing ringing in the impulse response. For this value of Q, the formula $\omega_c=2\pi k_Q f_c$ sets the –6 dB point of the filter at frequency $f_c=0.5$ Hz with factor $k_Q=1.325$.

The highpass filter 208 can be implemented digitally using a second-order difference equation of the form:

$$a_0 y_{HP}(n) = b_0 x(n) + b_1 x(n-1) + b_2 x(n-2) - a_1 y_{HP}(n-1) - a_2 y_{HP}(n-2)$$

where x(n) and $y_{HP}(n)$ are the signal input and output of the highpass filter 208 at sample time n, respectively. The filter response is determined by the coefficients $a_i$ and $b_j$. The highpass filter 208 can employ the Bilinear Transform to produce a digital filter that approximates the analog model, as it can provide very close matching of analog filter responses, particularly in their passband and transition bands. The resulting digital filter coefficients are as follows:

TABLE 2

| | |
|---|---|
| $a_0$ | 1.0 |
| $a_1$ | -1.97429463444953 |
| $a_2$ | 0.974632543411999 |
| $b_0$ | 0.987231794465383 |
| $b_1$ | -1.97446358893077 |
| $b_2$ | 0.987231794465383 |

The highpass filter 208 additionally provides a complementary lowpass filter output formed as the path difference between the input and output of the highpass filter 208, yielding in the sample domain, $y_{L\_HP}(n)=x(n)-y_{HP}(n)$. While the lowpass filter formed in this manner does not generally have particularly steep cutoff characteristics in its stopband, its group delay tends to match that of the highpass filter 208 in the transition band, thus working to preserve time alignment along the corresponding processing stages of the AC and DC signal paths for both the R and I signals.

The output $y_{HP}$ of the highpass filter 208 is tapped to make $x_{ac}$, forming the filtered AC component of the raw PPG signals (both R and I) from which the modulation amplitudes are estimated. As this waveform contains the pulsatile component of the PPG signal, it may also be used for estimation of the pulse rate PR. This signal may itself also be used to display a clean, zero-centered PPG waveform (e.g., on the display 120, such as a bedside monitor or central nursing station as described in U.S. Publication No. 2015/0302539). Usually, the filtered AC component resulting from the I signal would be used for this purpose as the I signal is typically larger in amplitude.

The output $y_{L\_HP}$ of the complementary lowpass is tapped to make $x_{LP}$, forming a time-aligned, partially-separated DC component, and so serves advantageously as the input to the lowpass filter 210 by providing some initial lowpass attenuation of AC components above fc with almost no additional computational cost.

The dedicated linear-phase lowpass smoothing filter 210 separates the DC component of the up-sampled/bandlimited PPG signal. The lowpass filter 210 is designed to remove all residual pulsatile and transient components from the raw PPG signal, so as to provide the moving-average, time-local value representing the raw optical transmission in the PPG signal. In addition, its time delay is aligned to match that of the corresponding processing path of the AC component. The lowpass filter 210 is implemented using a scaled integrator kernel, resulting in a computationally-efficient realization.

As shown in FIGS. 1 and 2, the AC processing path includes the AC-component highpass filter 208, along with the analytic wavelet bank 106 and the QP-domain harmonic detection and tracking unit 108, before appearing at the input of the QP-domain harmonic state vector filtering and amplitude statistics processing unit 110, where processing of the AC component occurs in combination with the separated DC component. According to the principles described previously regarding minimizing transients due to underlying signal changes, the intrinsic delays of the AC and DC processing paths to the QP-domain harmonic state vector filtering and amplitude statistics processing unit 110 are designed to both be equal. These delays, respectively $D_{ac}$ and $D_{dc}$ from the input x of the interpolation unit 204 of FIG. 2 to the QP-domain harmonic state vector filtering and amplitude statistics processing unit 110 of FIG. 1, are as follows:

$$D_{ac}=D_{ITP}+D_{HP}+D_{BNK}$$

$$D_{dc}=D_{ITP}+D_{HP}+D_{LP}$$

where $D_{BNK}$ is the intrinsic delay of the analytic wavelet bank 106, $D_{HP}$ is the group delay of the highpass filter 208 of the input processing and band separation unit 104, and $D_{LP}$ is the intrinsic delay of the DC component lowpass filter 210 of the input processing and band separation unit 104. The DC path delay includes $D_{HP}$ because the input of the DC component lowpass filter 210 is taken from the complementary-lowpass output $x_{LP}$ of the highpass filter 208 as described above. The QP-domain harmonic detection and tracking unit 108 is a memoryless operation and so has effectively a zero intrinsic delay. Thus, for $D_{ac}$ and $D_{dc}$ to be equal, $D_{LP}=D_{BNK}$. The scale of the DC component lowpass filter 210 to satisfy this is determined from the delay by the formula:

$$w_p=2 \cdot D_{LP}/N_i+1$$

which is integer-valued as long as $2 \cdot D_{LP}$ is an integer multiple of the order $N_i$, and is ensured an integer if $N_i=2$ and $D_{LP}$ is also an integer. As will be discussed below, in one example, the analytic wavelet bank 106 has intrinsic delay $D_{BNK}=1833$. For a processing sample rate of $F_s=225$ Hz, the parameters for the lowpass filter 210 would be as follows:

TABLE 3

| $w_p$ | $N_i$ | $D_{LP}$ |
|---|---|---|
| 1834 | 2 | 1833 |

The −6 dB lowpass cutoff for the lowpass filter 210 is $F_c=k_{6\ dB} \cdot F_s/w$, or 0.0543 Hz in this example, which can result in almost complete attenuation of pulsatile components and very effective DC smoothing (note that $k_{6\ dB}=0.44295$ for Ni=2). The output of the lowpass filter 210 is the moving estimate of the raw DC transmission component of the PPG signals, both R and I, time aligned to the moving modulation amplitude estimates for purposes of normalization and subsequent processing.

Referring to FIG. 1, the analytic wavelet bank 106 processes the resulting AC component of the PPG signal. The analytic wavelet bank 106 performs separation of the AC components into $n_B$ component bands each with substantially increased SNR. As described in U.S. Pat. Nos. 7,706,992 and 9,530,425, the analytic wavelet bank 106 separates the input AC signal into quasi-periodic components, each of which contains information that is significantly bandlimited relative to the input signal bandwidth. As a result, those bands containing information associated with local periodicities contained in the input signal will present that information with increased SNR.

The analytic wavelet bank 106 can be designed as a bank of bandpass filters with adjacently-spaced band centers. Each bandpass filter responds by varying amounts to periodicities present in the bank input signal according to its frequency response, having the greatest output amplitude for frequencies closest to the center frequency of the bandpass. For a bank input signal containing (quasi) periodic components, the filters substantially having the greatest output amplitude at a point in time, relative to their neighbors, will be those frequency bands with centers closest to the frequencies of those signal components. A tracing of the band amplitudes as a function of band frequency at that time point would reveal "peaks" at those associated frequencies. Finding and tracking these amplitude peaks as a function of time, along with the underlying information in the bands indexed by those peaks, forms the underlying principle for the design of the analytic wavelet bank 106. Another advantage of using bandpass filters is that each filter in the bank has relatively narrow bandwidth, thus having generally higher SNR relative to the associated frequency component.

A design consideration for the analytic wavelet bank 106 is the so-called "time-frequency frame" of the system 100, controlled through the "Q" (relative bandwidth) of the bandpass filters. Closely tied to the time-frequency frame is the frequency spacing of the bands. Excess band overlap decreases the selectivity between adjacent bands, which tends to "blur" the sharpness of the spectral peak for identifying the associated component. However, insufficient band overlap can lead to an excess of amplitude loss in the crossover region between band centers, leaving "holes" in the spectral representation of the signal, and in extreme cases leading to ambiguity in the spectral peak patterns. Higher Q will create a narrower filter bandwidth, allowing filters to be more closely spaced in frequency for a given amount of band overlap, thus providing increased frequency resolution. However, implementing a narrow filter bandwidth may require having an impulse response that is wider in time, which in turn translates to lower time resolution. Hence, the choice of Q represents a tradeoff between frequency resolution and time resolution.

As described in U.S. Pat. No. 9,530,425, the processing in QP space allows for time-frequency information to be captured with much higher precision in both time and frequency than conveyed by simply using the center frequency of a given band as the rate estimate. This property relaxes the requirement for frequency resolution among the band centers strictly to resolve frequency. In theory, a minimum of two bands per octave would be needed to isolate the fundamental harmonic from the second harmonic of the input periodic component, though in practice more bands may be required for low inter-band response crossover loss.

A wavelet support (impulse response length) approximately 3 cycles long may provide a good combination of both frequency isolation for components and adequately fast response times to resolve expected time dynamics associated with variabilities in pulse rates. An inter-band crossover dip level of less than −0.5 dB from the band centers may provide sufficient amplitude accuracy in representing the component amplitudes for pulse oximetry. Accordingly, the band spacing may be set to 9 bands per octave.

The analytic wavelet bank 106 can be implemented using an augmented form of the Parallel-Form Kovtun-Ricci Wavelet Transform with analytic component bands as described in U.S. Pat. No. 7,706,992. The wavelets are composed of a cascade of scaled-derivative kernels and scaled-integral kernels. The scaled-derivative kernel has a z-domain transfer function:

$$H_{dp}(Z) = [0.5(1 - Z^{-k_p})]^{N_{dp}}$$

having scale parameter $k_p$ and order parameter $N_{dp}$ for band p.

In addition to the scaled integral and scaled difference kernels, the analytic wavelet bank 106 can include in the kernel cascade an additional kernel type referred to here as a scaled comb kernel, having a z-domain transfer function:

$$H_{cp}(z) = \left[ \frac{1 - z^{-2k_p c_p}}{c_p(1 - z^{-2k_p})} \right]^{N_{cp}}$$

with scale parameters $k_p$ and $c_p$, and order parameter $N_{cp}$ for band p. The intrinsic delay of this kernel is $D_{cp} = N_{cp} \cdot k_p \cdot (c_p - 1)$. The frequency response of the scaled comb kernel for $N_{cp} = 1$ is a Dirichlet function, which closely approximates a sinc function at its first mainlobe around DC and then repeats these mainlobes over frequency at an interval controlled by scale parameter $k_p$ (specifically, at a frequency spacing of $F_s/(2 k_p)$ where $F_s$ is the processing sample rate). The value $k_p$ here is set by design to the same scaling value $k_p$ as appears in the expression for the scaled difference kernel. This centers the first repeated mainlobe of the scaled comb kernel over the first mainlobe of the scaled difference kernel, defining a new, more selective bandpass function centered at the peak of the mainlobe.

The scaled comb kernel features response nulls to either side of each repeated mainlobe, spaced away from each center according to scale parameter $c_p$, such that for $c_p = 2$ the nulls are halfway between the mainlobe centers, and for larger $c_p$, the nulls move proportionally closer to the mainlobe centers. These nulls have the effect of narrowing the mainlobe bandwidth, effectively increasing the Q of the filter. The Q is also increased with increasing order $N_{cp}$, so this kernel features two parameters by which Q may be controlled. Performance may be further enhanced in that the increased Q obtained due to the added side nulls, even for $c_p = 2$, results in less impulse response widening than when obtaining a similar Q via increasing scaled-derivative filter order alone. On the other hand, increasing the order may reduce the height of the sidelobes between the mainlobe images, and so the order $N_{cp}$ becomes a means to control stopband rejection in the regions just beyond the first passband nulls.

In a broadband sense, the scaled comb kernel acts as a comb filter, i.e., with a lobe around DC and repeating lobes according to scale $k_p$. To obtain a pure bandpass response, the first repeat of the mainlobe response above DC, which is centered at frequency $F_s/(2 k_p)$, may be isolated. To reject the lobe at DC, the scaled difference kernel is utilized, as it has a primary response null at DC. The scaled integral kernel is then utilized to reject the mainlobe images above the first, as well as to provide overall smoothing of the impulse response. Using these two kernels in the role of stopband rejection tends to not require high orders in practice (e.g., order 4 typically can provide sufficient out-of-band rejection).

The parameters for programming the bandpass wavelet responses are therefore $k_p$, $c_p$, $N_{cp}$, $N_{dp}$, $w_p$, and $N_{ip}$. For the pth bandpass, $k_p$ controls the center frequency and Q is controlled by the combination of (primarily) $c_p$, and (secondarily) $N_{cp}$ and scaled-derivative order $N_{dp}$. The parameters $N_{cp}$ and $N_{dp}$ control the stopband rejection near DC, and scaled-integral scale $w_p$ and order Nip control the stopband rejection above the passband.

As described in U.S. Pat. No. 7,706,992, scale parameter $k_p$ of the transform wavelet controls the frequency of the peak of the fundamental bandpass lobe, while scale parameter $w_p$ determines the frequency of the first null of the lowpass. Choosing the nominal value of $w_p \approx 2 k_p/3$ places that first null approximately at the peak of the second bandpass lobe of $H_{cp}(z)$, i.e. the first repeat of the comb, thus effectively isolating the fundamental bandpass response. Integral-order parameter $N_{ip}$ controls the degree of stopband attenuation for the lowpass operation; a value of $N_{ip} = 4$ may provide effective performance at low computational load.

Derivative-order parameter $N_{dp}$ controls the bandwidth of the bandpass function. For a filter bank, it controls the amount of overlap between the band responses. The values of $N_{dp}$ may be chosen so that the sum of the band responses is approximately flat over the power band, so that the total power of the complex is represented in a relatively unbiased fashion with regard to frequency.

This family of bandpass wavelets is computationally efficient and features linear phase response. As described in U.S. Pat. No. 7,706,992, the transform is implemented with time alignment across the bands to preserve timing information of the underlying component as it varies in rate across bands.

In accordance with the above descriptions and derivations, and for the sampling period as specified previously for the PPG signals, the bandpass wavelets of the analytic wavelet bank 106 can be implemented using the following design parameters:

TABLE 4

| Band | $F_{Cp}$ nominal (BPM) | $k_p$ | $c_p$ | $N_{cp}$ | $N_{dp}$ | $w_p$ | Nip |
|---|---|---|---|---|---|---|---|
| 1 | 27.92 | 234 | 2 | 4 | 4 | 157 | 4 |
| 2 | 29.98 | 218 | 2 | 4 | 4 | 145 | 4 |
| 3 | 32.37 | 202 | 2 | 4 | 4 | 134 | 4 |
| 4 | 35.14 | 186 | 2 | 4 | 4 | 124 | 4 |
| 5 | 37.99 | 172 | 2 | 4 | 4 | 115 | 4 |
| 6 | 40.86 | 160 | 2 | 4 | 4 | 106 | 4 |
| 7 | 44.15 | 148 | 2 | 4 | 4 | 99 | 4 |
| 8 | 48.04 | 136 | 2 | 4 | 4 | 91 | 4 |
| 9 | 51.83 | 126 | 2 | 4 | 4 | 85 | 4 |
| 10 | 55.42 | 118 | 2 | 4 | 4 | 78 | 4 |
| 11 | 60.52 | 108 | 2 | 4 | 4 | 72 | 4 |
| 12 | 65.33 | 100 | 2 | 4 | 4 | 67 | 4 |
| 13 | 69.58 | 94 | 2 | 4 | 4 | 62 | 4 |
| 14 | 75.94 | 86 | 2 | 4 | 4 | 58 | 4 |
| 15 | 81.73 | 80 | 2 | 4 | 4 | 53 | 4 |
| 16 | 88.36 | 74 | 2 | 4 | 4 | 49 | 4 |
| 17 | 96.02 | 68 | 2 | 4 | 4 | 46 | 4 |
| 18 | 102.2 | 64 | 2 | 4 | 4 | 42 | 4 |
| 19 | 112.6 | 58 | 2 | 4 | 4 | 39 | 4 |
| 20 | 121.0 | 54 | 2 | 4 | 4 | 36 | 4 |
| 21 | 130.5 | 50 | 2 | 4 | 4 | 34 | 4 |
| 22 | 142.0 | 46 | 2 | 4 | 4 | 31 | 4 |
| 23 | 148.6 | 44 | 2 | 4 | 4 | 29 | 4 |
| 24 | 163.3 | 40 | 2 | 4 | 4 | 27 | 4 |
| 25 | 181.0 | 36 | 2 | 4 | 4 | 25 | 4 |
| 26 | 192.1 | 34 | 2 | 4 | 4 | 23 | 4 |
| 27 | 204.5 | 32 | 2 | 4 | 4 | 21 | 4 |
| 28 | 217.9 | 30 | 2 | 4 | 4 | 20 | 4 |
| 29 | 234.0 | 28 | 2 | 4 | 4 | 18 | 4 |
| 30 | 251.7 | 26 | 2 | 4 | 4 | 17 | 4 |
| 31 | 272.4 | 24 | 2 | 4 | 4 | 16 | 4 |
| 32 | 298.0 | 22 | 2 | 4 | 4 | 14 | 4 |
| 33 | 327.4 | 20 | 2 | 4 | 4 | 13 | 4 |
| 34 | 363.2 | 18 | 2 | 4 | 4 | 12 | 4 |

TABLE 5

| Band | $K_{CR}$ | $K_{CI}$ |
|---|---|---|
| 1 | 2.1062922 | 2.1089759 |
| 2 | 2.0793090 | 2.0818756 |
| 3 | 2.0711782 | 2.0737073 |
| 4 | 2.0863364 | 2.0889356 |
| 5 | 2.0953176 | 2.0979586 |
| 6 | 2.0671799 | 2.0696907 |
| 7 | 2.0967443 | 2.0993922 |
| 8 | 2.0976443 | 2.1002965 |
| 9 | 2.1234868 | 2.1262615 |
| 10 | 2.0603402 | 2.0628197 |
| 11 | 2.0861533 | 2.0887516 |
| 12 | 2.1016212 | 2.1042917 |
| 13 | 2.0536938 | 2.0561430 |
| 14 | 2.1223712 | 2.1251407 |
| 15 | 2.0668054 | 2.0693145 |
| 16 | 2.0651836 | 2.0676854 |
| 17 | 2.1319122 | 2.1347275 |
| 18 | 2.0383987 | 2.0407796 |
| 19 | 2.1123333 | 2.1150548 |
| 20 | 2.0853243 | 2.0879190 |
| 21 | 2.1483483 | 2.1512437 |
| 22 | 2.1188631 | 2.1216159 |
| 23 | 2.0502374 | 2.0526714 |
| 24 | 2.1235371 | 2.1263125 |
| 25 | 2.2192235 | 2.2224760 |
| 26 | 2.1297798 | 2.1325855 |
| 27 | 2.0360882 | 2.0384593 |
| 28 | 2.0828502 | 2.0854340 |
| 29 | 1.9771225 | 1.9792380 |
| 30 | 2.0238779 | 2.0261950 |
| 31 | 2.0808389 | 2.0834138 |
| 32 | 1.9476177 | 1.9496107 |
| 33 | 2.0038989 | 2.0061295 |
| 34 | 2.0764990 | 2.0790548 |

The values $F_{Cp}$ are the center frequencies of the bands, defined as the frequency where the $p^{th}$ band exhibits its peak amplitude response. The frequency range covers sufficient range to resolve the required range of fundamental pulse rates (30 to 240 BPM) as well as the needed coverage to resolve a third harmonic at up to 120 BPM. As described above, the bands are spaced at nominally 9 bands per octave, so that full coverage of the desired rate range is achieved with 34 bands. The time-domain impulse response resulting for this wavelet order features an effective time length of approximately 3 cycles, and so represents good time resolution for locally-cyclic behavior.

Figure 3A:
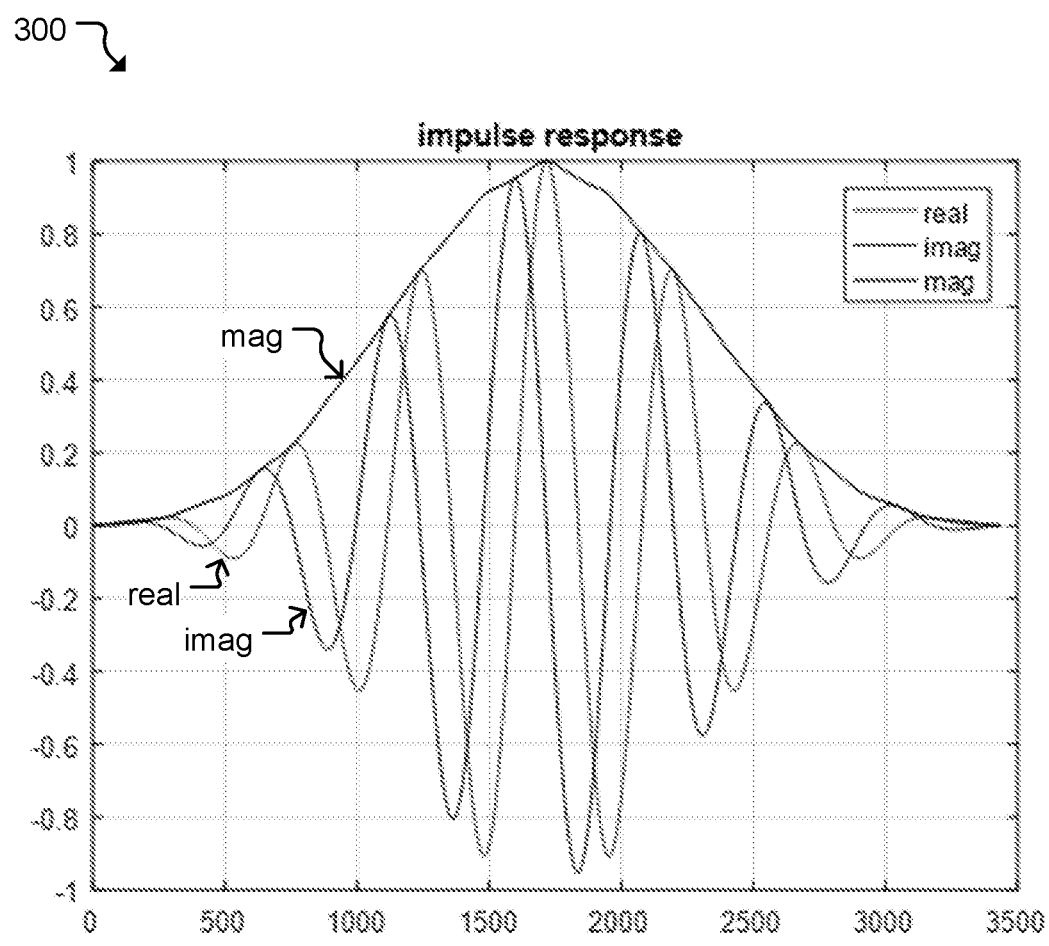
FIG. 3a is a plot showing an impulse response for one band of an analytic wavelet bank.
Figure 3B:
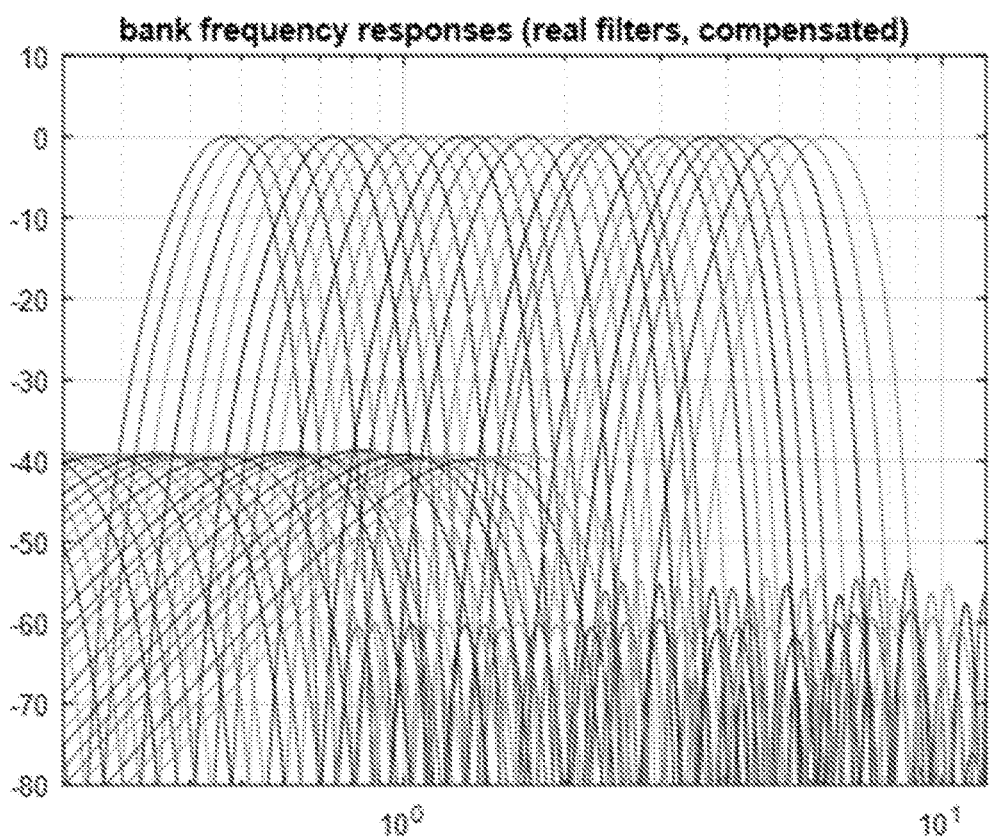
FIG. 3b is a plot showing frequency responses for the real part of the analytic wavelet bank.

FIG. 3a is a plot 300 showing the impulse response resulting from implementing the above parameters for the first band of the filter bank. Since the wavelets are analytic, the impulse responses are complex-valued. The "real" and "imag" traces are the real and imaginary parts of the impulse response, respectively. The "mag" trace is the instantaneous complex magnitude at each time point. FIG. 3b is a plot 350 showing frequency responses for the real part of the analytic wavelet bank.

To ensure calibration of the relative responses across the filter bank, the band output signals are normalized to unity gain at the band centers. Calibration factors $K_{CR}$ and $K_{CI}$ are determined by evaluating the real-part and imaginary-part amplitude responses (respectively) at their center frequencies $F_{Cp}$ and taking the multiplicative inverse. The real and imaginary filter outputs can be multiplied by their respective calibration factors, resulting in a calibrated filter bank. Accordingly, the calibration factors for each corresponding band are as follows:

Referring to FIG. 1, the QP-domain harmonic detection and tracking unit 108 performs QP transformation and state vector generation, robust periodicity detection for estimation of per-QP pulse interval $PI_{QP}$ based upon harmonic pattern identification in QP state space, and tracking of harmonic parameters in QP space for $n_H$ harmonics. Through a QP transform, the detection and tracking unit 108 analyzes the quasi-periodic components of the pulsatile signal to extract critical amplitude and local phase/frequency parameters occurring at QP update points, producing a time-frequency QP state vector. The QP update points are points in time associated with intrinsic information updates in the signal and occur naturally at rates much lower than the underlying sample rate of the signal.

The detection and tracking unit 108 detects QP transitions on each of the component signals, and forms, at each transition, an associated QP object as described in U.S. Pat. No. 7,706,992. For purposes of PPG processing, the QP objects contain the phase value (signified by a phase label), the time value and the component amplitude at the time point of QP detection, along with the index of the band for the underlying component. Collecting the current QPs at the current time point into an array across the bands forms a QP state vector, indexed by band, and updated upon any QP object update on any band as described in U.S. Pat. No. 7,706,992. The concentrated time-frequency information contained in this state vector forms the basis to enable the identification and tracking of desired signal components, and the high-precision estimation of their instantaneous frequencies and amplitudes.

The detection and tracking unit 108 further enhances SNR by identifying, selecting, and tracking the QP state information associated with the desired signal. The QP state vector provides instantaneous amplitude information over both frequency and time (e.g., a time-frequency analysis) that can be analyzed for patterns with which to identify and distinguish desired signals and artifacts. The current state of the associated QP amplitudes, taken across the frequency bands, forms a QP state spectrum whose peaks are associated with time-local quasi-periodic components. Such component peaks associated with a desired signal include the pulse rate and its harmonics (the pulse harmonic train), while other peaks may be associated with other quasi-periodic artifacts such as those arising from respiration (at the breath rate) and/or from repetitive motion.

The detection and tracking unit 108 analyzes the pattern of peaks in the QP state spectrum to identify only those peaks associated with the desired signal by taking advantage of the desired signal's typically harmonic pattern and the fact that other quasi-periodic artifacts tend to have harmonics of either low or unstable amplitude above the fundamental. Transients in the input signal appear over multiple bands simultaneously and/or tend to be relatively short in time, and so are either rejected outright or are suppressed through filtering in the tracking process.

After peak detection, the detection and tracking unit 108 ranks the peaks by size for forming measures upon them. To save computation time, only the first three peaks may be kept for harmonic-train analysis, as any peaks beyond this would be either from harmonics (and so already part of a harmonic train) or from lower-level artifacts. For similar reasons, only those peaks of these highest-ranked three with amplitude at least a minimum fraction of the first (largest) peak may be qualified for further analysis. This fraction may be set to 0.35. Under normal, high-SNR conditions, only one peak may qualify, so this peak may be used directly as the detected period.

Otherwise, for each remaining qualified peak, the QP amplitude spectrum is sampled at bands corresponding to that peak and to the harmonic frequencies of that peak. This train of QP amplitudes is then summed together, thus forming the harmonic-train amplitude measure (HTA), one for each qualified peak. As discussed above, three harmonics may be used in the computation. Where band indices for harmonics fall above the bands provided, as may happen for higher-frequency fundamental peaks, the amplitude contributions of those harmonics are set to zero. These HTAs are again ranked according to the measure, with only the largest two kept.

The detection and tracking unit 108 then applies a set of Peak-Pair Amplitude-Measure rules to this pair of HTA to select the one most associated with the desired signal. In one implementation, the set of rules is as follows:
If larger peak has higher frequency band
    Accept this peak (smaller, lower-rate peak is likely an artifact)
Otherwise (lower-rate peak is largest: check absolute, relative rate rules)
    If largest peak has band with rate above Upper Breath Rate Band Limit
        Accept this peak (rate is too high to be breath artifact)
    Otherwise, check band centers of peak pair for harmonic relationship
        Compute peak centroids (interpolated peaks)
        Compare interpolated band centroids for harmonic pattern
            Frequency ratio in region of 2/1 or 3/1
            Ratio within 1.2 bands @ 9 bands per octave
        If band relationship is harmonic Compare pair of harmonic train measure amplitudes
            If smaller peak is <0.9*larger peak
                Accept larger peak (smaller peak is likely 2nd harmonic)
            Otherwise
                Accept smaller peak (larger peak likely artifact at PR/2)
        Otherwise (band relationship is not harmonic)
            If smaller peak is >0.62*larger peak
                Accept smaller peak (peak large enough to be pulse)
            Otherwise
                Accept larger peak (smaller peak likely artifact)

In the above rules, the Upper Breath Rate Band Limit may correspond to band 12 at 65 BPM (a rate corresponding to an upper limit of hyperventilation). In the case that only one peak occurs in the spectrum, this peak is accepted by default. In the case that no peaks occur in the spectrum, the largest-amplitude band in the spectrum may be accepted as the peak.

To compute the peak centroids in the above rules, the detection and tracking unit 108 computes an interpolated band-index using a centroid (center-of-mass) computation. The central band is computed as the band-by-band sum of the product of band indices and corresponding band amplitudes divided by the band-by-band sum of the band amplitudes. The bands used in the computation include the peak band and the straddling bands. If the straddling bands satisfy a symmetry criterion, then they are both used along with the peak band. If not, then the largest of the straddling bands is used along with the peak band.

The symmetry criterion is defined as the absolute difference in the amplitudes of the straddling bands divided by the mean of those amplitudes (i.e., an amplitude-similarity measure equivalent to a Bland-Altman measure). This measure is compared to a threshold, which may be set to a value of 0.1 (i.e., a similarity of +/−10%), and similarity is declared if the measure is no more than this threshold value.

The detection and tracking unit 108 uses the accepted HTA to select the band upon which it is based, which is in turn associated with the fundamental of the pulse period. The detection and tracking unit 108 then uses the QP state information associated with this band and its harmonic bands to update a QP harmonic state vector dedicated to tracking the QP information for these $n_H$ harmonics. Harmonics with band indices past the upper limit are flagged as such for appropriate treatment in the QP-domain harmonic state vector filtering and amplitude statistics processing unit 110.

Updates to the QP harmonic state information are indicated by an advance in the QP time index accompanied by a change in the phase label (indicating a phase advance) in any of the contained harmonics. These updates are detected for each harmonic of each of the I and R channels, at which points corresponding amplitude and interval statistics are updated. For forming stable amplitude statistics, the QP amplitudes are individually smoothed through scaled integral kernels operating in QP space. The integral scales are set to a number of QP's that naturally match the underlying wavelet scale support for the fundamental cardiac cycle. For the system 100, this translates to 2.5 cardiac cycles, or 10 QP's at 4 QP's per cycle for the fundamental period. For the harmonics, the scale is increased proportionally with the harmonic number. This causes the harmonics to all closely follow the same time support, so that the smoothing is effectively synchronized over the same time scale for all harmonics. At QP updates where the harmonic is flagged as being out of bank range, the input to the amplitude smoothing is set to zero. Second-order scaled integral kernels may provide sufficient smoothing at this stage.

The tracked band corresponding to the lowest harmonic has frequency information corresponding to the fundamental period of the PPG pulse wave and thus the pulse interval (PI). The detection and tracking unit 108 of the I channel determines the pulse interval estimate by computing the instantaneous period of the fundamental harmonic, referred to as the QP "atomic period." Extracting this atomic period provides the pulse interval $PI_{QP}$ at each QP update. As described in U.S. Pat. No. 7,706,992, this is based upon computing time and phase differences from one QP update to the next of this particular component, which in turn yields information about the period of the underlying frequency component with high precision. The QP atomic period in this case is expressed as follows:

$$PI_{QP}=dT_{QP}/dP_{QP}$$

The value $PI_{QP}$ corresponds to the (instantaneous) atomic pulse interval in units of seconds-per-cycle. The value $dT_{QP}$ corresponds to the time interval from the previous QP update to the current one, in units of seconds, for the fundamental harmonic. The value $dP_{QP}$ corresponds to the advance in phase value associated with the number of quarter-phase labels that were traversed from the previous QP State update to the current one, and can be evaluated according to the following table:

TABLE 6

| Number of QP phase labels traversed | Description of QP State Transition | Phase change $dP_{QP}$ (in units of cycles) |
| --- | --- | --- |
| 0 | No change | 0 |
| 1 | Basic phase advance | 0.25 |
| 2 | Phase advance with skip | 0.5 |
| −1 | Phase reversal | −0.25 |

The number of QP phase labels traversed corresponds to the increment encountered along the cyclic sequence . . . A→B→C→D→A . . . in the current QP state transition, as described in U.S. Pat. No. 9,530,425. The basic phase advance (e.g., an increment of one) is the most common phase change. A phase change of zero is possible if the current QP update is associated with a change in selected fundamental band that happens to update to the same phase label as that of the selected fundamental band at the preceding QP. A phase label change of 2 is similarly possible with a change in selected fundamental band, but with an inversion of phase from the previous band to the next. Phase reversal is typically associated with transients in the signal, or with bands located far from any significant periodic components and thus exhibiting low relative band amplitude. The system 100 can be designed to mitigate both of these undesirable conditions, thus making phase reversal a highly unlikely transition type to be encountered.

The detection and tracking unit 108 may then update the atomic pulse interval $PI_{QP}$ at each QP update of the fundamental harmonic according to the following conditions and rules:

If $PI_{QP}$ is an invalid floating-point number (Inf, NaN) or is negative
  Force $PI_{QP}$ to the period corresponding to the center frequency of the selected fundamental wavelet band
Otherwise, if $PI_{QP}$ corresponds to a center frequency at least one wavelet band above or below the selected fundamental wavelet band
  Force $PI_{QP}$ to the period corresponding to the center frequency of the wavelet band above or below the selected fundamental wavelet band, respectively
Otherwise, $PI_{QP}$ is qualified as computed above A tracking update can be defined to occur upon a QP update of the fundamental harmonic.

As shown in FIG. 1, the detection and tracking unit 108 of the I channel provides $PI_{QP}$ and associated band index information to the detection and tracking unit 108 of the R channel. The fundamental pulse-related periodicity information underlying the pulse modulation is essentially common to both PPG signals, as the timing of the modulations is primarily related to the cardiac cycle and the mechanics of perfusion. Hence, the identification of the bands for the harmonic pattern may be computed on one channel (the "master"), and the associated band-selection information then passed to the other channel (the "slave") and used for harmonic-tracking purposes. In the system 100, the I channel is the master, as it typically exhibits higher SNR. The bands of the QP state vector that are associated with the desired pulse harmonic train thus contain concentrated, high SNR time-varying amplitude and phase/frequency information sufficient to represent (and/or reconstruct) each harmonic of the pulse modulation component of the PPG signal, and by extension, the modulation component of the PPG signal itself.

The process of periodicity detection and period-band selection occurs at each QP state update of the I channel, as does the updating of its QP harmonic state vector. The QP harmonic state vector for the R channel is updated at each QP state update of the R channel, and uses the current period-band that is selected at that update time. The detection and tracking unit 108 provides the two QP harmonic state vectors to the QP-domain harmonic state vector filtering and amplitude statistics processing unit 110.

The system 100 includes a pulse interval (PI) filter 112 that performs QP-synchronized filtering to generate an instantaneous pulse interval $PI_{inst}$. To maintain time alignment in the reported pulse rate, the pulse interval $PI_{QP}$ is processed with the same QP time-based filtering/smoothing operation, e.g., smoothed through a scaled integral kernel with the same parameters as that applied to the fundamental harmonic QP amplitude, as used in the QP-domain harmonic state vector filtering and amplitude statistics processing unit 110, updated upon each QP update of the first harmonic to produce the instantaneous pulse interval $PI_{inst}$ synchronized to the smoothed harmonic amplitudes.

The QP-domain harmonic state vector filtering and amplitude statistics processing unit 110 performs individual per-harmonic filtering of parameters (QP-space linear smoothing) to form robust moving measures of the harmonic amplitude, QP-synchronized filtering of the DC component of the PPG signal, combination of the harmonic amplitude to form robust measure of the AC component pulse amplitude, and combination of the AC component pulse amplitude with the DC information to form robust moving measures ($A_{NI}$ for the I signal path, $A_{NR}$ for the R signal path) of the normalized percent-fraction PPG pulse modulation. The QP-domain harmonic state vector filtering and amplitude statistics processing unit 110 filters individually the QP amplitude parameters for each harmonic to provide time-based smoothing of statistics for general suppression of variability and noise at the output of the tracking process. The separated DC components, $I_{dc}$ and $R_{dc}$, of the PPG signals are smoothed through parallel scaled integral kernels, with the same parameters as that applied to the fundamental harmonic QP amplitude, and updated at the same QP updates. This produces smoothed DC components $I_{dcs}$ and $R_{dcs}$ synchronized to the smoothed harmonic amplitudes.

By filtering each harmonic individually, the amplitude associated with each fine aspect of the morphology can be smoothed independently, adding independent robustness against interference that may occur in bands neighboring a particular harmonic. Additionally, as these harmonic state filters are updated independently upon each individual harmonic's QP update, computational savings may be realized relative to per-sample filtering, especially on the lower harmonics as the QP update rates scale proportionally to frequency. In order to maintain time alignment between the AC and DC components, the unit 110 may also sample the DC components of the PPG signal at each QP update of the first harmonic (the fundamental), and process them using the same QP time-based filtering/smoothing operation.

The unit 110 combines the smoothed harmonic amplitudes to form robust moving estimates of the amplitude of the AC component, i.e., the pulse amplitude of the PPG signal. At each tracking update, the smoothed statistics can be combined as follows. The smoothed harmonic amplitudes for each PPG channel are linearly combined to form moving estimates $a_{IR}$ and $a_R$ of the AC components corresponding to the PPG pulse amplitudes. The linear combination weights applied to the smoothed harmonic amplitudes need not be uniform. Reducing the weight on the first harmonic works to suppress the effect of artifacts, which tend to influence the lowest harmonic the most at low SNRs, without significantly impacting performance at higher SNRs. Weights for the linear combination may be as follows, in order of harmonic number: 0.125, 1.0, 1.0.

The moving estimates $a_{IR}$ and $a_R$ are then normalized by the corresponding smoothed DC component value, resulting in robust moving measures of the normalized percent-fraction PPG pulse modulation, shown as $A_{NI}$ and $A_{NR}$ in FIG. 1. The moving measures of the normalized percent-fraction PPG pulse modulations $A_{NI}$ and $A_{NR}$ are computed at each tracking update as follows:

$$A_{NI} = a_R/I_{dcs}$$

$$A_{NR} = a_R/R_{dcs}$$

The system 100 includes a division unit 114 that provides the moving measure $R_N$ of the normalized modulation ratio of $A_{NI}$ and $A_{NR}$. The normalized modulation ratio $R_N = A_{NR}/A_{NI}$, which forms the instantaneous moving measure from which SpO$_2$ is mapped.

The system 100 includes statistical filters 116a and 116b. Statistical filter 116a forms smoothed moving estimates $R_{PPG}$ of the normalized modulation ratio $R_N$. Statistical filter 116b forms smoothed moving estimates $PI_{PPG}$ of instantaneous pulse interval $PI_{inst}$. Each statistical filter performs statistically-based smoothing, based upon a moving stack filter, to provide a final smoothing function and to remove any remaining large, outlying transient excursions from the final output. Identical smoothing filters are applied to both $R_N$ and $PI_{inst}$ in parallel to generally preserve time alignment, resulting in final moving PPG measures $R_{PPG}$ and $PI_{PPG}$.

The statistical filters 116a and 116b are designed to remove any remaining large, outlying transient excursions from the final outputs and to generally stabilize the output readings. An averaging time $T_{stat}=2.5$ seconds may produce an acceptable level of smoothing while keeping time lag as low as possible. Hence, at each tracking update, the averaging for each statistical filter 116a and 116b is updated using the respective values of $R_N$ and $PI_{inst}$ occurring within the interval $T_{stat}$ seconds preceding (and including) the current tracking update. Rather than performing simple moving averages, smoothed medians are computed by taking the averages of the central values, in a percentile sense, over a range around the pure medians. The central-range average may be set to include those values in the inter-quartile range centered around the median value, to preserve robustness against outliers while also producing well-smoothed outputs over time. By using the same parameters and update times, synchronization may be preserved between the two smoothed output statistics.

The system 100 includes mapping units 118a and 118b. Mapping unit 118a performs mapping of $R_{PPG}$ to output SpO$_2$ values. Mapping unit 118b performs mapping of $PI_{PPG}$ to output pulse rate PR values.

The normalized modulation ratio $R_{PPG}$ can be mapped to SpO$_2$ through a polynomial function, for example a second-order polynomial. The polynomial coefficients may be determined through a calibration procedure, e.g., by collecting SaO$_2$ and corresponding $R_{PPG}$ values at a hypoxia lab from subjects following a standard ramp-down protocol, then performing a second-order fit to form the map to SpO$_2$. Various probes may be supported, for example finger probes and ear probes, by collecting $R_{PPG}$ values using each probe and then forming separate corresponding maps for each.

The polynomial is evaluated as follows:

$$y = \sum_{n=0}^{2} a_n x^n$$

where $R_{PPG}$ is the input value x, and output y is the mapped value of SpO$_2$. In one implementation, the values an are as follows for finger and ear probes:

TABLE 7

| N | $a_n$ (Finger Probe) | $a_n$ (Ear Probe) |
|---|---|---|
| 0 | 112.02185 | 115.49644 |
| 1 | −21.632549 | −27.554501 |
| 2 | −4.2294321 | −3.3103607 |

To prevent excess excursion in output values, the SpO$_2$ output value range may be limited to an upper value of 100% and a lower value of 0%.

The instantaneous Pulse Interval $PI_{PPG}$ is typically mapped to the pulse rate PR through the following formula:

$$PR = 60 \cdot F_s/PI_{PPG}$$

where the Pulse Interval is expressed in samples and PR in BPM. To prevent excess excursion in output values, the PR output value range may be limited to an upper value of 240 BPM and a lower value of 30 BPM.

Local losses in signal amplitude may occur due to complete signal loss, such as due to lead detachment, or from lack of pulse modulation, such as due to extremely low perfusion or due to cardiac pause or asystole. Because SpO$_2$ and PR are not well-defined under these conditions, the system 100 includes an output qualification unit 122 that uses the amplitude level of the normalized modulation signal to qualify the pulse modulation amplitude for sufficient level to support confidence in desired accuracy. This amplitude level may be based upon forming a moving estimate $I_{ama}$ of the amplitude of AC component $I_{ac}$ along with a time-aligned moving estimate $I_{md}$ from DC component $I_{dc}$ and comparing the ratio of these values to a threshold, placed at the point where performance is observed experimentally to drop significantly.

The moving AC amplitude estimate $I_{ama}$ and DC component estimate $I_{md}$ are formed by smoothing the absolute value of AC component $I_{ac}$ and DC component $I_{dc}$ respectively with moving average filters. The filters may be implemented with scaled integral cascades having the same parameters, thus having linear phase with time alignment between the estimates. The smoothing may be set as second order with a time scale of 3 seconds, to sufficiently smooth pulsatile components from the estimates while still maintaining time-responsiveness to drops and rises in amplitude. For the processing sample rate of $F_s$=225 Hz, the following scaled-integral parameters may be used for the smoothing filters:

TABLE 8

| $w_{sm}$ | $N_i$ | $D_{sm}$ |
|---|---|---|
| 675 | 2 | 674 |

A flag $f_{sig}$, which is asserted for normalized modulation signal amplitude levels generally above a confidence threshold, and de-asserted below, is used for qualifying the signal level for pulse oximetry. In cases where the signal level moves through the threshold value slowly with small ripples superimposed, chattering of the qualification flag could result. This can be mitigated by adding hysteresis to the threshold (e.g., inversely relating the threshold to the qualification state). Also, due to the time lag inherent in the various processing stages, time delay may be added to the assertion and de-assertion of the flag so that the indication of signal quality aligns in time with the output readings of the pulse oximetry.

The output qualification unit 122 can meet both of these objectives by implementing the signal-qualification process with a state machine. The state definitions and state-transition rules are as follows:

Initialization: State=NOT_QUAL//$f_{sig}$=False

TABLE 9

| Current State | Condition | Next State//Action |
|---|---|---|
| NOT_QUAL | $I_{ama}/I_{md}$ > threshU | WAIT_UP//Reset Wait_Count |
| WAIT_UP | $I_{ama}/I_{md}$ < threshD (Else) | NOT_QUAL (Else) |
|  | Wait_Count > TdelayU | QUAL//$f_{sig}$ = True |
| QUAL | $I_{ama}/I_{md}$ < threshD | WAIT_DN//Reset Wait_Count |
| WAIT_DN | $I_{ama}/I_{md}$ > threshU (Else) | QUAL (Else) |
|  | Wait_Count > TdelayD | NOT_QUAL//$f_{sig}$ = False |

The threshold values may be set as follows:

TABLE 10

| Thresholds (Upward, Downward) | Values |
|---|---|
| threshU | 0.00028 |
| threshD | 0.00014 |

The delay times may be set as follows:

TABLE 11

| Delays (Upward, Downward) | Values (seconds) |
|---|---|
| TdelayU | 22.5 |
| TdelayD | 5 |

The output qualification unit 122 provides the signal qualification flag $f_{sig}$ to an output interface 124 as a means of suppressing display of spurious or erroneous pulse oximetry output during unfavorable signal conditions. Delays may be chosen to cause de-assertion of flag $f_{sig}$ before deterioration of signal conditions and re-assertion of flag $f_{sig}$ after restoration of signal conditions, seeking to ensure favorable signal conditions only when flag $f_{sig}$ is asserted.

The system 100 can continuously display average $SpO_2$ values and average PR values on a display 120. The display 120 can be a display of a bedside monitor, a central server station, or a mobile device as described in U.S. Publication No. 2015/0302539. The display 120 can alert a user of the display 120 if an alarm state for the patient is detected. The display 120 can alert the user by, for example, flashing, changing color, becoming enlarged, or otherwise visually indicating an alarm state. For example, if the patient's $SpO_2$ level increases to above an upper acceptable bound or decreases to a lower acceptable bound, the display 120 can flash to indicate an alarm state to a user of the display 120. The system 100 can alert the user by triggering an audible alarm. In some implementations, different audible alarms can be used to indicate different alarm states or severity of an alarm state. The volume of an audible alarm can also be used to indicate the relative severity of an alarm state.

The system 100 can also alert users to an alarm state by causing one or more portions of the display 120 to flash, issuing an audible alarm, or transmitting alerts to other devices. For example, a bedside monitor can transmit an alert to a central server which can then identify one or more caregivers to whom to direct the alert associated with a patient. The central server can then transmit alerts to devices associated with the identified caregivers.

The pulse oximetry system 100 can be useful in any setting where a patient's oxygenation is unstable, including intensive care, operating, recovery, emergency and hospital ward settings, pilots in unpressurized aircraft, for assessment of any patient's oxygenation, and determining the effectiveness of or need for supplemental oxygen. The system 100 can provide continuous and immediate oxygen saturation values, which are of critical importance in emergency medicine and are also very useful for patients with respiratory or cardiac problems, especially chronic obstructive pulmonary disease (COPD), or for diagnosis of some sleep disorders such as apnea and hypopnea.

In some implementations, the system 100 can be implemented as a portable battery-operated pulse oximeter. Such portable battery-operated pulse oximeters are useful for pilots operating in a non-pressurized aircraft above 10,000 feet (12,500 feet in the U.S.) where supplemental oxygen is required. Portable pulse oximeters are also useful for mountain climbers and athletes whose oxygen levels may decrease at high altitudes or with exercise. Portable pulse oximeters can employ the system 100 to monitor a patient's blood oxygen and pulse, serving as a reminder to check blood oxygen levels.

Figure 4:
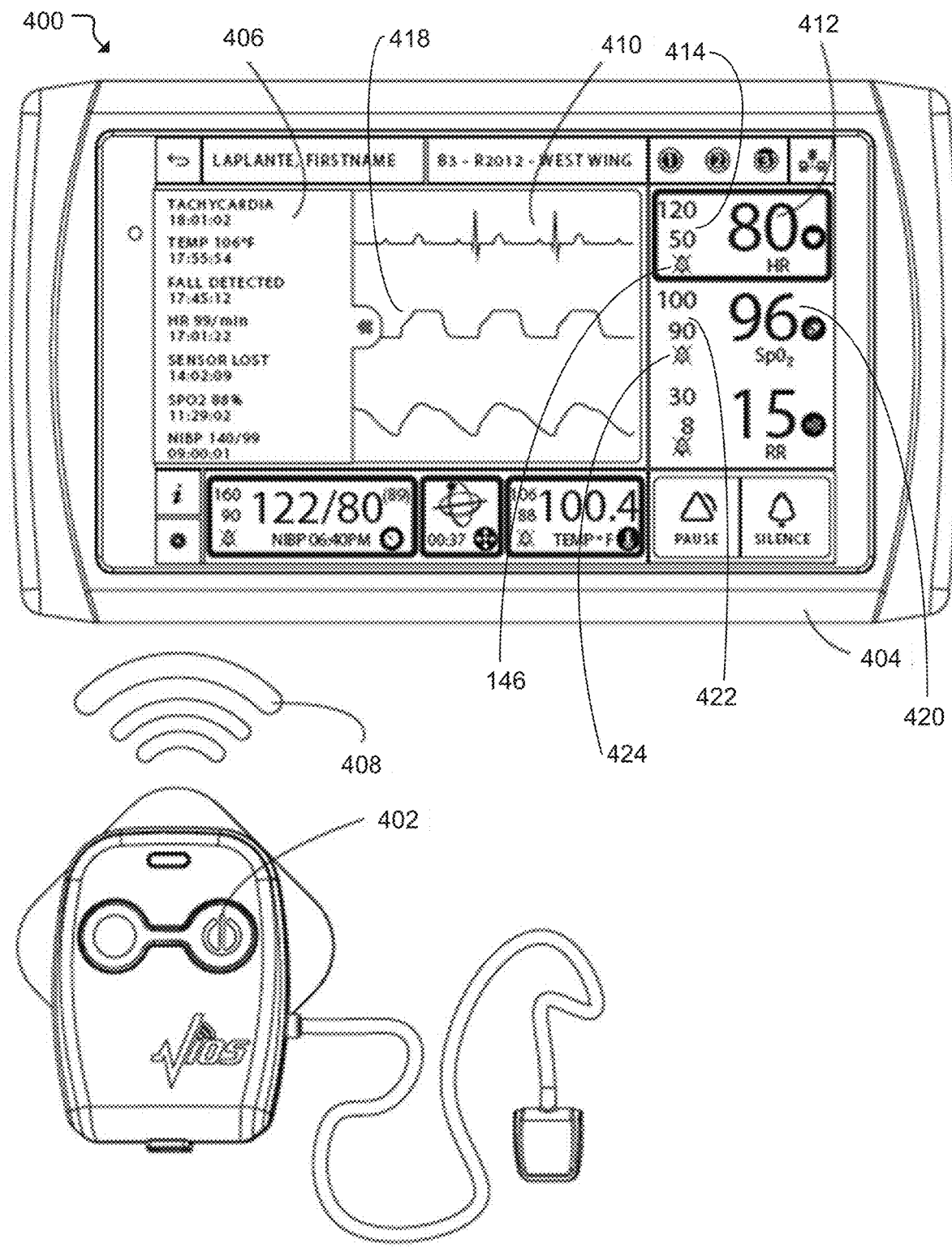
FIG. 4 shows an example of a pulse oximetry system that includes a patient worn sensor in communication with a display device.

FIG. 4 shows a system 400 that includes a patient worn sensor 402 in communication with a display device 404, such as a display of a bedside monitor, a central server station, or a mobile device as described in U.S. Publication No. 2015/0302539. The display device 404 displays information for a patient. The display device 404 can display a user interface 406 that includes information received from the patient worn sensor 402 and/or information associated with a patient associated with the patient worn sensor 402. The patient worn sensor 402 can be, for example, a chest sensor as described in U.S. Publication No. 2015/0302539. The patient worn sensor 402 can include contacts for attaching to the skin of a patient and recording various patient vital signs such as blood pressure, body temperature, respiratory rate, body impedance, blood oxygenation, heart rhythm (via ECG), and heart rate.

The patient worn sensor 402 can wirelessly communicate with the display device 404 through a wireless connection 408 using a wireless communication protocol such as, for example, Bluetooth, WiFi, or a cellular protocol. The patient worn sensor 402 can transmit vital sign information for the patient to the display device 404 through the wireless connection 408. In some implementations, the patient worn sensor 402 can perform processing on the collected vital sign information prior to transmission of the information to the display device 404, while in some implementations, the patient worn sensor 402 can transmit raw vital sign information to the display device 404 instead of or in addition to processed information. The display device 404 can be a touch screen device, such as a tablet, that is capable of receiving touch screen inputs. In some implementations, the display device 404 can receive input from a keyboard, mouse, input buttons, or one or more devices capable of recognizing voice commands. In some implementations, the display device 404 can be controlled using a device in wireless communication with the display device 404, such as a mobile phone. In some implementations, the display device 404 is a "headless" device that does not include direct user input and/or output functionality, but rather merely serves as a processing device for processing raw vital sign information received from the patient worn sensor 402, detecting alarm states, transmitting alerts to other devices in communication with the display device 404, and transmitting patient information to one or more central servers. In such cases, the display device 404 would not include a display.

The user interface 406 displays information for a patient associated with the patient worn sensor 402. For example, electrodes of the patient worn sensor 402 can be in contact with the patient's skin and collect vital sign information which is transferred to the display device 404 through the wireless connection 408, processed by the display device 404, and displayed as part of the user interface 406. The user interface 406 shows various vital sign waves and numeric levels.

For example, the user interface 406 shows a heart rate waveform 410 for the patient as well as a numeric heart rate or pulse rate value 412 for the patient. In the example shown, the pulse rate value 412 for the patient is 80 beats per minute. The user interface 406 indicates at 414 an acceptable heart rate level for the patient as falling between 50 and 120 beats per minute. Being as the current heart rate for the patient of 80 beats per minute falls within the indicated acceptable range, there is not currently an alarm state for heart rate for the patient. This is indicated by an icon 416 of a bell superimposed with an "X" symbol. The icon 416 indicates that the current heart rate of the patient is within the acceptable range. In a situation in which the heart rate for the patient is not within the acceptable level, the icon 416 can change to indicate an alarm state. For example, the "X" can disappear from the icon 416 and the icon 416 can light up or flash to indicate an alarm state. Additionally, the display device 404 can emit an audible alarm to alert nearby caregivers to an alarm state for the patient. In some implementations, other portions of the user interface 406 can flash or otherwise indicate an alarm state. For example, the displayed pulse rate value 412 can flash when the patient's pulse rate is outside of an acceptable level. In some implementations, the icon 416 (or other portions of the user interface 406) can flash at varying rates to indicate the severity of a particular alarm state. For example, the icon 416 can flash faster the further the patient's heart rate is from the acceptable range.

The user interface 406 shows a blood oxygenation waveform 418 and a numeric blood oxygenation value 420 for the patient. The user interface 406 also shows, at 422, an acceptable blood oxygenation range for the patient. The user interface 406 further includes an icon 424 indicating that the blood oxygenation level for the patient is within the acceptable range (indicated by an "X" symbol superimposed over a bell, indicating that the alarm is "off").

Figure 5:
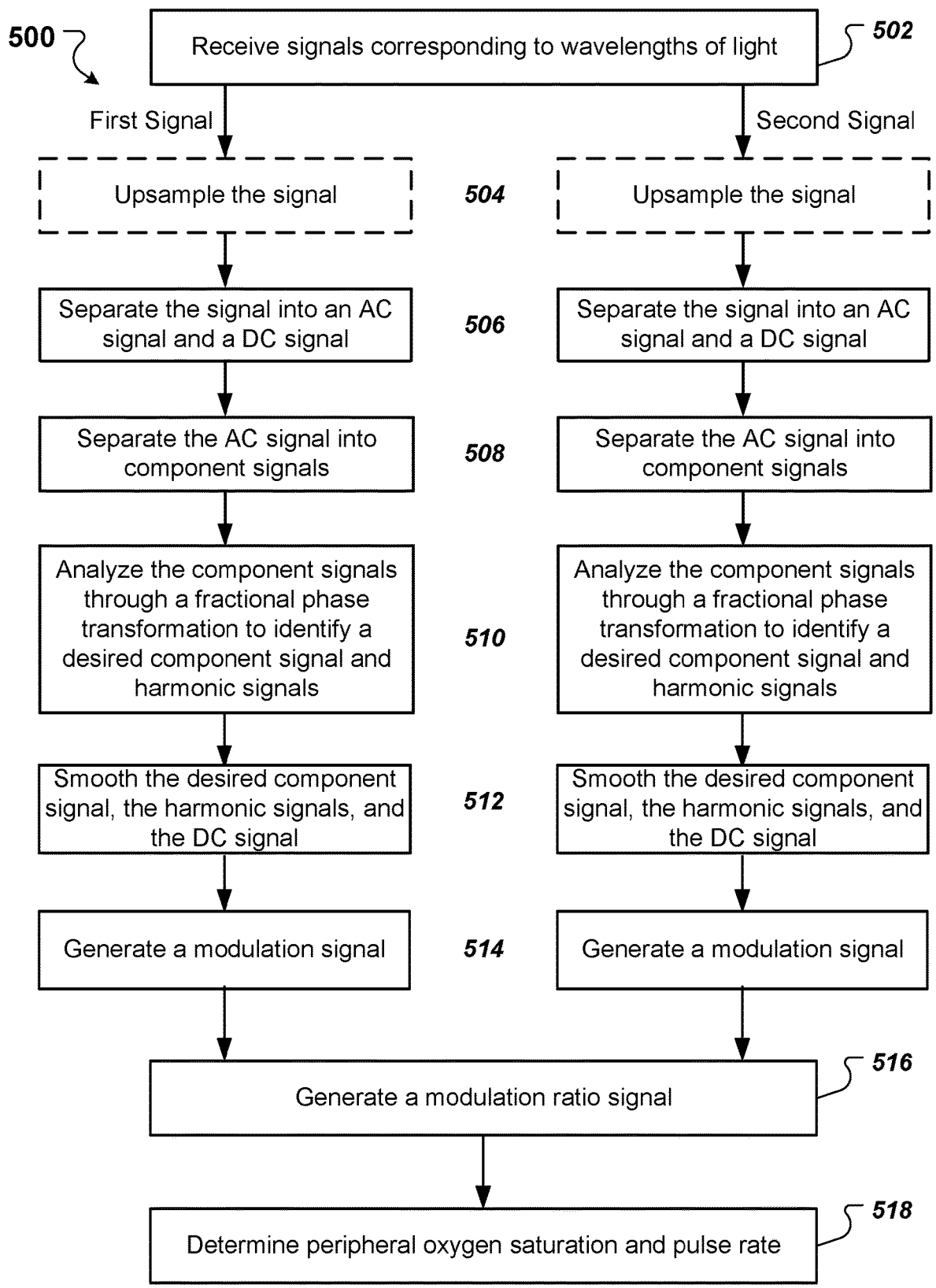
FIG. 5 is a flowchart showing examples of operations performed by a pulse oximetry system.

FIG. 5 is a flowchart showing examples of operations 500 performed by a pulse oximetry system. The operations 500 may be performed by a system of one or more computers, such as the system of FIG. 1. The operations 500 may include details that have been discussed above.

At 502, the system receives signals corresponding to wavelengths of light detected by an optical sensor placed in proximity to a patient's body. The signals include a first signal corresponding to a first wavelength of light detected by the optical sensor and a second signal corresponding to a second wavelength of light detected by the optical sensor.

Operations 504 through 514 are performed for each received signal of the first signal and the second signal. At 504, the signal is optionally upsampled to increase the sample rate. At 506, the signal is separated into an AC signal and a DC signal.

At 508, the AC signal is separated into component signals, where each of the component signals represents a frequency-limited band. Separating the AC signal into the component signals may include filtering the AC signal using a bank of bandpass filters having adjacently-spaced band centers and normalizing outputs of the bank of bandpass filters to generate the component signals.

At 510, the system analyzes the component signals through a fractional phase transformation to identify a desired component signal and harmonic signals associated with the desired component signal. To identify the desired component signal and the harmonic signals, the system may determine an atomic period by computing an instantaneous period of a lowest harmonic signal derived from the first signal. For the first signal, the desired component signal and the harmonic signals may be identified based on the atomic period and by analyzing time-aligned amplitude values of the component signals and the relationships of amplitudes of the harmonic signals. Based on the atomic period, the system may determine an atomic pulse interval, and the desired component signal and the harmonic signals for the second signal may be identified based on the atomic pulse interval.

At 512, the system smooths the desired component signal, the harmonic signals, and the DC signal. At 514, the smoothed desired component signal, the smoothed harmonic signals, and the smoothed DC signal are combined to generate a modulation signal. Combining the smoothed desired component signal, the smoothed harmonic signals, and the smoothed DC signal may include linearly combining the smoothed desired component signal and the smoothed harmonic signals to generate a combined signal, and normalizing the combined signaled using the smoothed DC signal to generate the modulation signal.

At 516, the system generates a modulation ratio signal based on the modulation signal derived from the first signal and the modulation signal derived from the second signal. At 518, the peripheral oxygen saturation ($SpO_2$) of the patient's body is determined based on the modulation ratio signal. Determining the $SpO_2$ of the patient's body may include generating smoothed moving estimates of the modulation ratio signal and mapping the smoothed moving estimates to output values representing the $SpO_2$ of the patient's body. The system may also determine a pulse rate of the patient's body based on the atomic pulse interval determined above.

Figure 6:
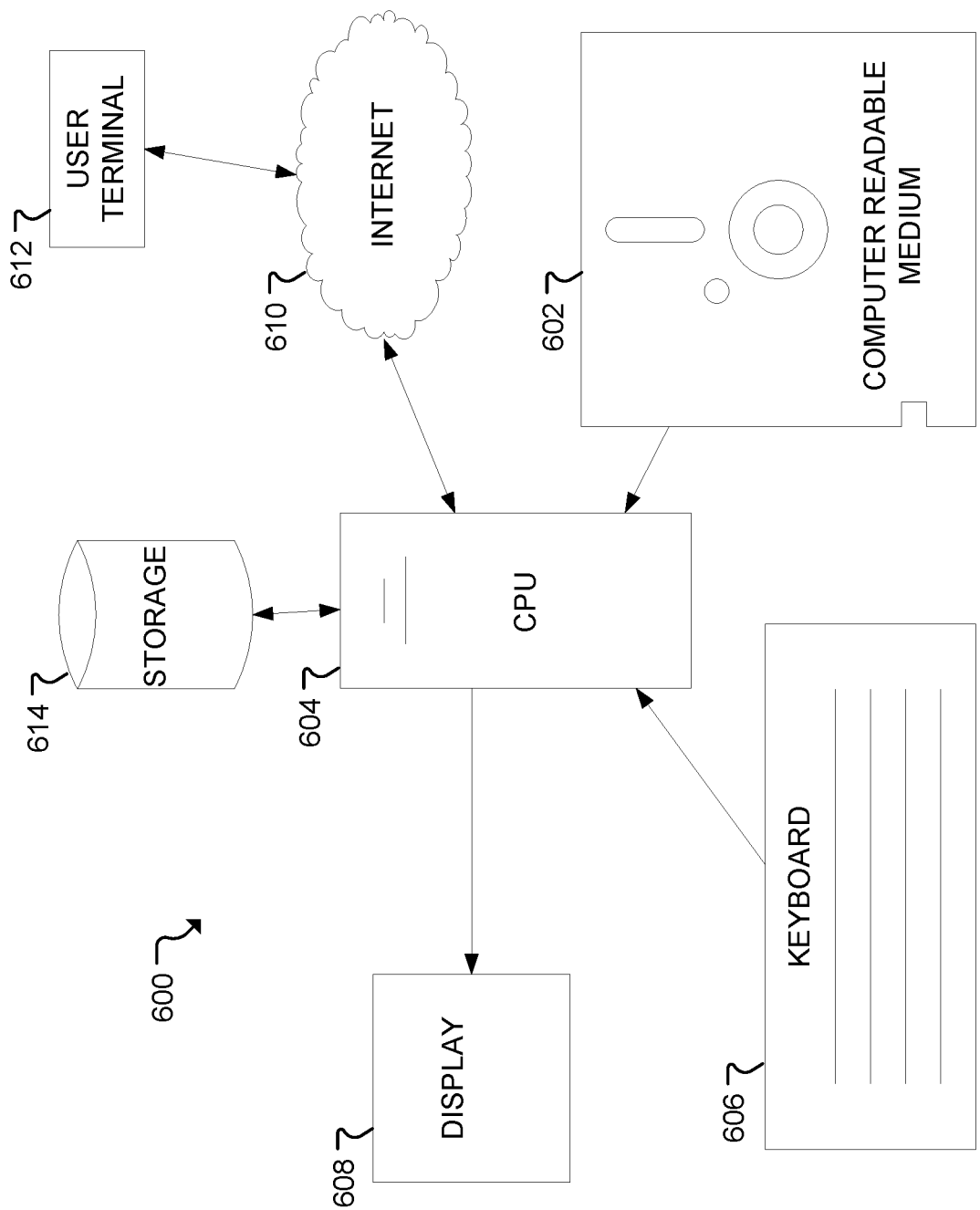
FIG. 6 is a block diagram showing an example of a computing system that may be used to implement a pulse oximetry system.

FIG. 6 is a block diagram showing an example of a computing system 600 executing a computer program that implements the above-described operations, data structures, and/or programs contained on a computer readable medium 602, and executed by a central processing unit (CPU) 604. The CPU 604 may be an x86 series CPU or other CPU known in the art. Input to execute the program can, in some implementations, come by way of a keyboard 606. In some implementations, input to execute the program can come by way of a peripheral device such as a mouse, light pen, touch screen, touch pad, or any other input device known in the art. In some implementations, the described operations can be called by another program to execute and process oximetry data. Once processed, data processed using the above-described operations, data structures, and/or programs can be outputted to a display 608, or sent via an internet 610 or other wireless communications channel to another user terminal 612. In some implementations, the output can be placed into a database 614 or another database located off-site.

Figure 7:
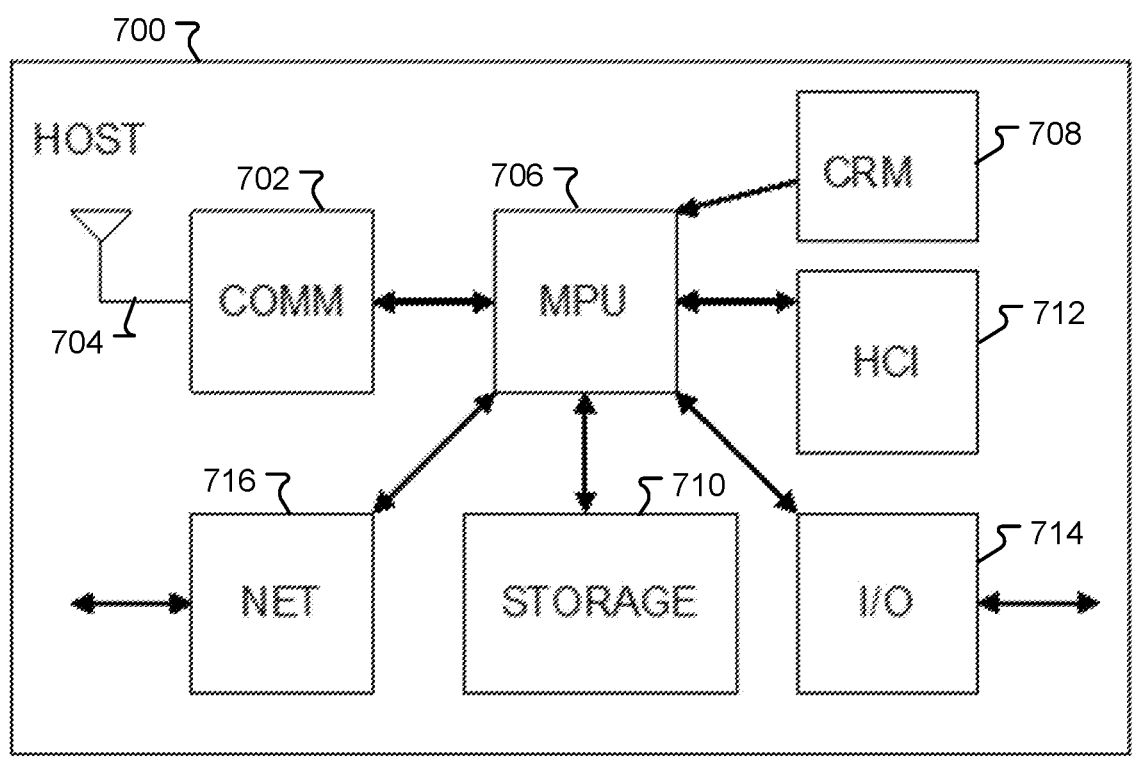
FIG. 7 is a block diagram showing an example of a computing system that depicts a host system that may be used to implement a pulse oximetry system.

FIG. 7 is a block diagram showing an example of a computing system that depicts a host 700 which may, in some implementations, include a set of units or modules such as a communications module 702 and associated communications link 704 for communicating with a patient worn sensor, a microprocessor unit 706 (MPU) including a computer readable medium 708 containing a set of application instructions, an associated storage module 710 for storing patient data, a Human-Computer Interface 712 by which an operator (e.g., a physician, technician, or patient) may interact with the MPU 706 and which may include a visual display, auditory display, keyboard, mouse, touch screen, haptic device, or other means of interaction. The host 700 also includes an input/output module 714 for generally connecting to, and communicating with, computer peripherals such as for example printers, scanners, and/or data acquisition or imaging equipment, and a network communications module 716 for communicating with other hosts on a computer network such as Ethernet and/or a wireless network, or WiFi.

The features described in this disclosure can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor, and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing context.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer area processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application specific integrated circuits). To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet. The computer system can include clients and servers. A client and server are generally remote from each other and typically interact through a network, such as the described one. The relationship of client and server arises by virtue of computer programs running on the respective computers and having a client-server relationship to each other.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as Such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software or hardware product or packaged into multiple software or hardware products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A non-transitory computer readable storage medium encoded with a computer program, the program comprising instructions that when executed by one or more data processing apparatus cause the one or more data processing apparatus to perform operations comprising:
   receiving a first signal corresponding to a first wavelength of light detected by an optical sensor placed in proximity to a patient's body;
   receiving a second signal corresponding to a second wavelength of light detected by the optical sensor;
   for each received signal of the first signal and the second signal:
      separating the signal into an AC signal and a DC signal;
      separating the AC signal into component signals, wherein each of the component signals represents a frequency-limited band,
      analyzing the component signals through a fractional phase transformation to identify a desired component signal and harmonic signals associated with the desired component signal,
      smoothing the desired component signal, the harmonic signals, and the DC signal, and
      combining the smoothed desired component signal, the smoothed harmonic signals, and the smoothed DC signal to generate a modulation signal;
   generating a modulation ratio signal based on the modulation signal derived from the first signal and the modulation signal derived from the second signal; and
   determining peripheral oxygen saturation ($SpO_2$) of the patient's body based on the modulation ratio signal.

2. The non-transitory computer-readable storage medium of claim 1, wherein:
   the operations further comprise, for each received signal of the first signal and the second signal, converting the received signal having a first sample rate to an upsampled signal having a second sample rate, the second sample rate being higher than the first sample rate; and
   separating the signal into the AC signal and the DC signal comprises separating the upsampled signal into the AC signal and the DC signal.

3. The non-transitory computer readable storage medium of claim 1, wherein for the first signal, identifying the desired component signal and the harmonic signals comprises analyzing time-aligned amplitude values of the component signals.

4. The non-transitory computer readable storage medium of claim 1, wherein for the first signal, identifying the desired component signal and the harmonic signals comprises analyzing relationships of amplitudes of the harmonic signals.

5. The non-transitory computer readable storage medium of claim 1, wherein:
   the operations further comprise determining an atomic period by computing an instantaneous period of the desired component signal.

6. The non-transitory computer readable medium of claim 5, wherein for the first signal, identifying the desired component signal and the harmonic signals comprises identifying the harmonic signals based the atomic period.

7. The non-transitory computer readable storage medium of claim 5, wherein:
   the operations further comprise determining an atomic pulse interval based on the atomic period.

8. The non-transitory computer readable storage medium of claim 7, wherein for the second signal, identifying the desired component signal and the harmonic signals is based on the atomic pulse interval.

9. The non-transitory computer readable storage medium of claim 7, wherein:
   the operations further comprise determining a pulse rate of the patient's body based on the determined atomic pulse interval.

10. The non-transitory computer readable storage medium of claim 1, wherein separating the AC signal into the component signals comprises:
    filtering the AC signal using a bank of bandpass filters having adjacently-spaced band centers; and
    normalizing outputs of the bank of bandpass filters to generate the component signals.

11. The non-transitory computer readable storage medium of claim 1, wherein combining the smoothed desired component signal, the smoothed harmonic signals, and the smoothed DC signal to generate a modulation signal comprises:
    linearly combining the smoothed desired component signal and the smoothed harmonic signals to generate a combined signal; and
    normalizing the combined signaled using the smoothed DC signal to generate the modulation signal.

12. The non-transitory computer readable storage medium of claim 1, wherein determining the $SpO_2$ of the patient's body based on the modulation ratio signal comprises:
    generating smoothed moving estimates of the modulation ratio signal; and
    mapping the smoothed moving estimates to output values representing the $SpO_2$ of the patient's body.

13. A computer-implemented method comprising:
    receiving a first signal corresponding to a first wavelength of light detected by an optical sensor placed in proximity to a patient's body;

receiving a second signal corresponding to a second wavelength of light detected by the optical sensor;

for each received signal of the first signal and the second signal:
  separating the signal into an AC signal and a DC signal;
  separating the AC signal into component signals, wherein each of the component signals represents a frequency-limited band,
  analyzing the component signals through a fractional phase transformation to identify a desired component signal and harmonic signals associated with the desired component signal,
  smoothing the desired component signal, the harmonic signals, and the DC signal, and
  combining the smoothed desired component signal, the smoothed harmonic signals, and the smoothed DC signal to generate a modulation signal;

generating a modulation ratio signal based on the modulation signal derived from the first signal and the modulation signal derived from the second signal; and determining peripheral oxygen saturation ($SpO_2$) of the patient's body based on the modulation ratio signal.

14. The computer-implemented method of claim 13, further comprising:
  for each received signal of the first signal and the second signal, converting the received signal having a first sample rate to an upsampled signal having a second sample rate, the second sample rate being higher than the first sample rate; and
  wherein separating the signal into the AC signal and the DC signal comprises separating the upsampled signal into the AC signal and the DC signal.

15. The computer-implemented method of claim 13, wherein for the first signal, identifying the desired component signal and the harmonic signals comprises analyzing time-aligned amplitude values of the component signals.

16. The computer-implemented method of claim 13, wherein for the first signal, identifying the desired component signal and the harmonic signals comprises analyzing relationships of amplitudes of the harmonic signals.

17. The computer-implemented method of claim 13, further comprising:
  determining an atomic period by computing an instantaneous period of the desired component signal.

18. The computer-implemented method of claim 17, wherein for the first signal, identifying the desired component signal and the harmonic signals comprises identifying the harmonic signals based the atomic period.

19. The computer-implemented method of claim 17, further comprising:
  determining an atomic pulse interval based on the atomic period.

20. The computer-implemented method of claim 19, wherein for the second signal, identifying the desired component signal and the harmonic signals is based on the atomic pulse interval.

21. The computer-implemented method of claim 19, further comprising:
  determining a pulse rate of the patient's body based on the determined atomic pulse interval.

22. The computer-implemented method of claim 13, wherein separating the AC signal into the component signals comprises:
  filtering the AC signal using a bank of bandpass filters having adjacently-spaced band centers; and
  normalizing outputs of the bank of bandpass filters to generate the component signals.

23. The computer-implemented method of claim 13, wherein combining the smoothed desired component signal, the smoothed harmonic signals, and the smoothed DC signal to generate a modulation signal comprises:
  linearly combining the smoothed desired component signal and the smoothed harmonic signals to generate a combined signal; and
  normalizing the combined signaled using the smoothed DC signal to generate the modulation signal.

24. The computer-implemented method of claim 13, wherein determining the $SpO_2$ of the patient's body based on the modulation ratio signal comprises:
  generating smoothed moving estimates of the modulation ratio signal; and
  mapping the smoothed moving estimates to output values representing the $SpO_2$ of the patient's body.

25. A system comprising:
  an optical sensor configured to light;
  a display apparatus;
  one or more data processing apparatus coupled with the optical sensor and the display apparatus; and
  a non-transitory computer readable storage medium encoded with a computer program, the program comprising instructions that when executed by the one or more data processing apparatus cause the one or more data processing apparatus to perform operations comprising:
    receiving a first signal corresponding to a first wavelength of light detected by the optical sensor placed in proximity to a patient's body;
    receiving a second signal corresponding to a second wavelength of light detected by the optical sensor;
    for each received signal of the first signal and the second signal:
      separating the signal into an AC signal and a DC signal;
      separating the AC signal into component signals, wherein each of the component signals represents a frequency-limited band,
      analyzing the component signals through a fractional phase transformation to identify a desired component signal and harmonic signals associated with the desired component signal,
      smoothing the desired component signal, the harmonic signals, and the DC signal, and
      combining the smoothed desired component signal, the smoothed harmonic signals, and the smoothed DC signal to generate a modulation signal;
    generating a modulation ratio signal based on the modulation signal derived from the first signal and the modulation signal derived from the second signal;
    determining peripheral oxygen saturation ($SpO_2$) of the patient's body based on the modulation ratio signal; and
    causing the display apparatus to display a value representing the determined $SpO_2$ of the patient's body.

26. The system of claim 25, wherein:
  the operations further comprise, for each received signal of the first signal and the second signal, converting the received signal having a first sample rate to an upsampled signal having a second sample rate, the second sample rate being higher than the first sample rate; and
  separating the signal into the AC signal and the DC signal comprises separating the upsampled signal into the AC signal and the DC signal.

27. The system of claim 25, wherein for the first signal, identifying the desired component signal and the harmonic signals comprises analyzing time-aligned amplitude values of the component signals.

28. The system of claim 25, wherein for the first signal, identifying the desired component signal and the harmonic signals comprises analyzing relationships of amplitudes of the harmonic signals.

29. The system of claim 25, wherein:
the operations further comprise determining an atomic period by computing an instantaneous period of the desired component signal.

30. The system of claim 29, wherein for the first signal, identifying the desired component signal and the harmonic signals comprises identifying the harmonic signals based the atomic period.

31. The system of claim 29, wherein:
the operations further comprise determining an atomic pulse interval based on the atomic period.

32. The system of claim 31, wherein for the second signal, identifying the desired component signal and the harmonic signals is based on the atomic pulse interval.

33. The system of claim 31, wherein:
the operations further comprise determining a pulse rate of the patient's body based on the determined atomic pulse interval.

34. The system of claim 25, wherein separating the AC signal into the component signals comprises:
filtering the AC signal using a bank of bandpass filters having adjacently-spaced band centers; and
normalizing outputs of the bank of bandpass filters to generate the component signals.

35. The system of claim 25, wherein combining the smoothed desired component signal, the smoothed harmonic signals, and the smoothed DC signal to generate a modulation signal comprises:
linearly combining the smoothed desired component signal and the smoothed harmonic signals to generate a combined signal; and
normalizing the combined signaled using the smoothed DC signal to generate the modulation signal.

36. The system of claim 25, wherein determining the $SpO_2$ of the patient's body based on the modulation ratio signal comprises:
generating smoothed moving estimates of the modulation ratio signal; and
mapping the smoothed moving estimates to output values representing the $SpO_2$ of the patient's body.

37. The non-transitory computer-readable storage medium of claim 1, wherein
the step of analyzing generates fractional-phase state vectors corresponding to the desired component signal and the harmonic signals,
the step of smoothing includes smoothing the fractional-phase state vectors, and
the step of combining includes combining the smoothed DC signal and the smoothed fractional-phase state vectors to generate the modulation signal.

38. The non-transitory computer-readable storage medium of claim 37, wherein
each of the fractional-phase state vectors is updated at each transition between fractional phases, and
each of the smoothed DC signal, the smoothed fractional-phase state vectors, and the modulation signal is updated when one of the fractional-phase state vectors is updated.

39. The computer-implemented method of claim 13, wherein
the step of analyzing generates fractional-phase state vectors corresponding to the desired component signal and the harmonic signals,
the step of smoothing includes smoothing the fractional-phase state vectors, and
the step of combining includes combining the smoothed DC signal and the smoothed fractional-phase state vectors to generate the modulation signal.

40. The computer-implemented method of claim 39, wherein
each of the fractional-phase state vectors is updated at each transition between fractional phases, and
each of the smoothed DC signal, the smoothed fractional-phase state vectors, and the modulation signal is updated when one of the fractional-phase state vectors is updated.

41. The system of claim 25, wherein
the step of analyzing generates fractional-phase state vectors corresponding to the desired component signal and the harmonic signals,
the step of smoothing includes smoothing the fractional-phase state vectors, and
the step of combining includes combining the smoothed DC signal and the smoothed fractional-phase state vectors to generate the modulation signal.

42. The non-transitory computer-readable storage medium of claim 41, wherein
each of the fractional-phase state vectors is updated at each transition between fractional phases, and
each of the smoothed DC signal, the smoothed fractional-phase state vectors, and the modulation signal is updated when one of the fractional-phase state vectors is updated.

* * * * *